US010426808B2

(12) United States Patent
Thangavel et al.

(10) Patent No.: US 10,426,808 B2
(45) Date of Patent: *Oct. 1, 2019

(54) PLANT EXTRACTS HAVING ANTICOCCIDIAL ACTIVITY

(71) Applicant: Kemin Industries, Inc., Des Moines, IA (US)

(72) Inventors: Gokila Thangavel, Hosur (IN); Rajalekshmi Mukkalil, Cochin (IN); Haridasan Chirakkal, Chennai (IN); Hannah Kurian, Bangalore (IN); Elke Schoeters, Mol (BE); Hilde Wouters, Zandhoven (BE); Ilse Mast, Lint (BE)

(73) Assignee: KEMIN INDUSTRIES, INC., Des Moines, IA (US)

( * ) Notice: Subject to any disclaimer, the term of this patent is extended or adjusted under 35 U.S.C. 154(b) by 741 days.

This patent is subject to a terminal disclaimer.

(21) Appl. No.: 14/802,545

(22) Filed: Jul. 17, 2015

(65) Prior Publication Data

US 2016/0015765 A1 Jan. 21, 2016

Related U.S. Application Data

(62) Division of application No. 13/928,504, filed on Jun. 27, 2013.

(60) Provisional application No. 61/664,795, filed on Jun. 27, 2012.

(30) Foreign Application Priority Data

Jan. 23, 2013 (IN) .............................. 177/DEL/2013

(51) Int. Cl.
*A61K 36/49* (2006.01)
*A61K 36/185* (2006.01)
*A61K 36/22* (2006.01)
*A61K 31/192* (2006.01)

(52) U.S. Cl.
CPC ............ *A61K 36/49* (2013.01); *A61K 31/192* (2013.01); *A61K 36/185* (2013.01); *A61K 36/22* (2013.01)

(58) Field of Classification Search
None
See application file for complete search history.

(56) References Cited

U.S. PATENT DOCUMENTS

2002/0019353 A1* 2/2002 Canning ............ A61K 31/7052
514/28
2010/0179151 A1 7/2010 Heep et al.

FOREIGN PATENT DOCUMENTS

| CN | 101407638 A | 4/2009 |
|---|---|---|
| CN | 101744839 | 6/2010 |
| CN | 101744839 A | 6/2010 |
| CN | 102988764 A | 3/2013 |
| EP | 0395294 | 10/1990 |
| EP | 0395294 A2 | 10/1990 |
| WO | 9613175 | 5/1996 |
| WO | 9613175 A1 | 5/1996 |

OTHER PUBLICATIONS

Yilmaz et al., "Major Flavonoids in Grape Seeds and Skins: Antioxidant Capacity of Catechin, Epicatechin, and Gallic Acid," Journal of Agricultural and Food Chemistry, 2004, vol. 52, pp. 255-260.
Banfield et al., "Effects of whole wheat dilution v. substitution on coccidiosis in broiler chickens," British Journal of Nutrition, 2001, vol. 85, pp. 89-95.
Hagerman et al., "Tannin chemistry in relation to digestion," Journal of Range Management, vol. 45 (1), Jan. 1992, pp. 57-62.
Nicholas-Orians, Colin, "Differential Effects of Condensed and Hydrolyzable Tannin on Polyphenol Oxidase Activity of Attine Symbiotic Fungus," Journal of Chemical Ecology, vol. 17, No. 9, 1991, pp. 1811-1819.
Rajora et al., "Phytochemical analysis and estimation of major bioactive compounds from *Triticum aestivum* L. grass with antimicrobial potential," Journal of Pharmaceutical Science, vol. 28, No. 6 (supp), Nov. 2015, pp. 2221-2225.
Wang et al., "Chemical characterization and antioxidant evaluation of muscadine grape pomace extract," Journal of Food Chemistry, vol. 123, 2010, pp. 1156-1162.
Hur et al., "Effects of Feeding Condensed Tannin-containing Plants on Natural Coccidian Infection in Goats," Asian-Aust. Journal of Animal Science, 2005, vol. 18, No. 9, pp. 1262-1266.
McDougald et al., "Enhancement of Resistance to Coccidiosis and Necrotic Enteritis in Broiler Chickens by Dietary Muscadine Pomace," Avian Diseases, vol. 52, No. 4, 2008, pp. 646-651.
Abbas et al., "Anticoccidial Activity of *Curcuma longa* L. In Broilers," Brazilian Archives of Biology and Technology: AN International Journal, vol. 59, No. 1, 2010, pp. 63-67.
Aivazi et al., "Larvicidal activity of oak *Quercus infectoria* Oliv. (Fagaceae) gall extracts against Anopheles stephensi Liston," Parasitol Res, vol. 104, 2009, pp. 1289-1293.
Allen et al., "Dietary modulation of avian coccidiosis," International Journal for Parasitology, vol. 28, 1998, pp. 1131-1140.
Attarde et al., "Estimation of Tannin Content in Some Marketed Harde Churna (Terminalia Chebula Retz, Family—Combretaceae)," International Journal of Pharmacy & Technology, vol. 2, Issue No. 3, Sep. 2010, pp. 750-756.
Basri et al., "In Vitro Antibacterial Activity of Galls of Quercus infectoria Olivier against Oral Pathogens," Evidence-Based Complementary and Alternative Medicine, vol. 2012, Article ID 632796, 2011, 6 pages.

(Continued)

*Primary Examiner* — Terry A McKelvey
*Assistant Examiner* — Catheryne Chen
(74) *Attorney, Agent, or Firm* — Nyemaster Goode P.C.

(57) ABSTRACT

Natural plant parts and extracts of plants selected from the group consisting of *Quercus infectoria*, *Rhus chinensis* and *Terminalia chebula* containing compounds such as gallic acid, derivative of gallic acid, gallotannins and hydrolysable tannins have been found to control coccidiosis in poultry and, more specifically, coccidiosis caused by *Eimeria* spp. The plant parts and natural extracts result in a reduction of lesion score, oocysts per gram of fecal matter and mortality.

13 Claims, 14 Drawing Sheets

(56) References Cited

OTHER PUBLICATIONS

Chandrakesan et al., "Efficacy of a herbal complex against caecal coccidiosis in broiler chickens," Journal of Veterinary Archives, vol. 79, No. 2, 2009, pp. 199-203.
Clare et al., Major Histocompatibility Complex Control of Immunity Elicited by Genetically Engineered Eimeria tenella (Apicomplexa) Antigen in Chickens, Journal of Infection and Immunity, vol. 57, No. 3, Mar. 1989, pp. 701-705.
Jang et al., "Anticoccidial effect of green tea-based diets against Eimeria maxima," Journal of Veterinary Parasitology, vol. 144, 2007, pp. 172-175.
Kaur et al., "Quercus infectoria galls possess antioxidant activity and abrogates oxidative stress-induced functional alterations in murine macrophages," Journal of Chemico-Biological Interactions, vol. 171, 2008, pp. 272-282.
Khazandi et al., "Developing an in vitro method for Eimeria tenella attachment to its preferred and non-preferred intestinal sites," Journal of Experimental Parasitology, vol. 125, 2010, pp. 137-140.
Lee et al., "Anticoccidial effects of Galla rhois extract on Eimeria tenella-infected chicken," Journal of Laboratory Animal Research,vol. 28, No. 3, pp. 193-197.
Leela et al., "Studies on the Antibacterial Activity of Quercus Infectoria Galls," 2011 International Conference on Bioscience, Biochemistry and Bioinformatics, vol. 5, 2011, 5 pages.
Naiddo et al., "The value of plant extracts with antioxidant activity in attenuating coccidiosis in broiler chickens," Journal of Veterinary Parasitology, vol. 153, 2008, pp. 214-219.
Nweze et al., "Anticoccidial effects of Ageratum conyzoides," Journal of Ethnopharmacology, vol. 122, 2009, pp. 6-9.
Rajeshwari et al., "Efficacy of DIAREX VET in Treating Rabbit Coccidiosis," The Veterinarian, vol. 27, Dec. 2003, pp. 12-13.
Rochfort et al., "Plant bioactives for ruminant health and productivity," Journal of Phytochemistry, vol. 69, 2008, pp. 299-322.
Lk et al., "Ultrastructural Findings and Elemental Analysis of Quercus infectoria Oliv," Annals of Microscopy, vol. 7, Apr. 2007, 6 pages.
Williams, R. B., "Intercurrent coccidiosis and necrotic enteritis of chickens: rational, integrated disease management by maintenance of gut integrity," Avian Pathology, vol. 34, No. 3, 2005, pp. 159-180.
Zhang et al., "Effects of ginger root (Zingiber officinale) processed to different particle sizes on growth performance, antioxidant status, and serum metabolites of broiler chickens," Journal of Poultry Science, vol. 88, 2009, pp. 2159-2166.
Allen et al., "Effects of Components of Artemisia annua on Coccidia Infections in Chickens," Journal of Poultry Science, vol. 76, 1997, pp. 1156-1163.
Aroonrerk et al., "Anti-Inflammatory Activity of Quercus Infectoria, Glycyrrhiza Uralensis, Kaempferia Galanga and Coptis Chinesis, The Main Components of Thai Herbal Remedies for Aphthous Ulcer," Journal of Health Res., vol. 23, No. 1, 2009, pp. 17-22.
Biu et al., "Use of neem (Azadirachta indica) aqueous extract as a treatment for poultry coccidiosis in Borno State, Nigeria," African Scientist, vol. 7, No. 3, Sep. 30, 2006, 7 pages.
Ghafour et al., "Determination of Some Chemical Constitutes of Oak Plants (Quercus spp) in the Mountain Oak Forest of Sulaimani Governorate," Journal of Zankoy Sulaimani, vol. 13, No. 1, 2010, pp. 129-142.
Jeurissen et al., "Eimeria tenella infections in chickens: aspects of host-parasite: interaction," Veterinary Immunology and Immunopathology, vol. 54, 1996, pp. 231-238.
Kiani et al., "Sources and Routes of Introduction of Eimeria Oocysts into Broiler Chick's Houses," International Journal of Poultry Science, vol. 6, No. 12, 2007, pp. 925-927.
Kitazato et al., "Viral infectious disease and natural products with antiviral activity," Drug Discoveries & Therapeutics, vol. 1, No. 1, 2007, pp. 14-22.
McCann et al., "The Use of Mannan-Oligosaccharides and/or Tannin in Broiler Diets," International Journal of Poultry Science, vol. 5, No. 9, 2006, pp. 873-879.

Molan et al., "Effect of pine bark (Pinus radiata) extracts on sporulation of coccidian oocysts," Folia Parasitologica, vol. 56, No. 1, 2009, pp. 1-5.
Sawangjaroen et al., "The effects of extracts from anti-diarrheic Thai medicinal plants on the in vitro growth of the intestinal protozoa parasite: Blastocystis hominis," Journal of Ethnopharmacology, vol. 98, 2005, pp. 67-72.
Sawangjaroen et al., "Effects of Piper longum fruit, Piper sarmentosum root and Quercus infectoria nut gall on caecal amoebiasis in mice," Journal of Ethnopharmacology, vol. 91, 2004, pp. 357-360.
Dv et al., "Pharmacological review on Terminalia Chebula," International Journal of Research in Pharmaceutical and Biomedical Sciences, vol. 3, No. 2, Apr.-Jun. 2012, pp. 679-683.
Wang et al., "Influence of Grape Seed Proanthocyanidin Extract in Broiler Chickens: Effect on Chicken Coccidiosis and Antioxidant Status," Journal of Poultry Science, vol. 87, 2008, pp. 2273-2280.
Rao Zahid Abbas et al., "Anticoccidial Activity of Curcuma longa L. in Broilers", "Brazilian Archives of Biology and Technology", 2010, pp. 63-67, vol. 53, No. 1, Published in: Brazil.
Ali-Ashraf Aivazi et al., "Larvicidal activity of oak Quercus infectoria Oliv. (Fagaceae) gall extracts against Anopheles stephensi Liston", "Parasitol Research", 2009, pp. 1289-1293, vol. 104.
Patricia Allen et al., "Dietary modulation of avian coccidiosis", "International Journal for Parasitology", 1998, pp. 1131-1140, vol. 28.
Patricia C. Allen et al., "Effects of Components of Artemisia annua on Coccidia Infections in Chickens", "Poultry Science", 1997, pp. 1156-1163, vol. 76.
Nuntana Aroonrerk et al., "Anti-inflammatory activity of Quercus infectoria, Glycyrrhiza uralensis, Kaempferia galanga and Coptis chinensis, the main components of thai herbal remedies for aphthous ulcer", "Journal of Health Research", 2009, pp. 17-22, vol. 23, No. 1.
Attarde et al., "Estimation of tannin content in some marketed harde Churna (terminalia chebula retz. family-combretaceae)", "International Journal of Pharmacy and Technology", 2010, pp. 750-756, vol. 2, No. 3.
Dayang Fredalina Basri et al., "In vitro antibacterial activity of galls of Quercus infectoria Olivier against Oral Pathogens", "Evidence-Based Complementary and Alternative Medicine", 2011, pp. 16, vol. 2012.
A. A. Biu et al., "Use of neem (Azadirachta indica) aqueous extract as a treatment for poultry coccidiosis in Borno State, Nigeria", "African Scientist", Sep. 30, 2006, pp. 147-153, vol. 7, No. 3, Published in: Nigeria, Africa.
Chandrakesan et al., "Efficacy of a herbal complex against caecal coccidiosis in broiler chickens", "Beterinarski Arhiv", Apr. 2, 2009, pp. 199-203, vol. 79, No. 2.
Robert A. Clare et al., "Major histocompatibility complex control of immunity elicited by genetically engineered Eimeria tenella (Apicomplexa) antigen in chickens", "Infection and Immunity", Mar. 1989, pp. 701-705, vol. 57, No. 3, Published in: US.
Noori Hassan Ghafour et al., "Determination of Some Chemical Constitutes of Oak Plants (Quercus spp) in the Mountain Oak Forest of Sulaimani Governorate", "Journal of Zankoy Sulaimani", 2010, pp. 129-142, vol. 13, No. 1.
T. Gokila, "Coccidiosis in vitro trial II", "Lab Record GT", Sep. 16, 2011, pp. 104-110.
T. Gokila, "In vitro screening of plant extracts for antisporozoidal activity—Part II", Dec. 4, 2011, p. 118.
T. Gokila et al., "In Vivo Screening of Plant Extracts for Anticoccidial Activity—Part II", "K Source WP—12—00017", 2012.
Sam Hur et al., "Effects of Feeding Condensed Tannin-containing Plants on Natural Coccidian Infection in Goats", "Asian-Australian Journal of Animal Sciences", Sep. 1, 2009, pp. 1262-1266, vol. 18, No. 9.
Jang et al., "Anticoccidial effet of green tea-based diets against Eimeria maxima", "Veterinary Parasitology", Oct. 5, 2006, pp. 172-175, vol. 144.
S.H.M. Jeurissen et al., "Eimeria tenella infections in chickens: aspects of host-parasite: interactions", "Veterinary immunobiology and immunopathology", 1996, pp. 231-238, vol. 54.

(56) References Cited

OTHER PUBLICATIONS

Gurpreet Kaur et al., "Quercus infectoria galls possess antioxidant activity and abrogates oxidative stress-Induced functional alterations in murine macrophages", "Chemico-Biological Interactions", 2008, pp. 272-282, vol. 171.

Manouchehr Khazandi et al., "Developing an in vitro method for Eimeria tenella attachment to its preferred and non-preferred intestinal sites", "Experimental Parasitology", Jan. 2010, pp. 137-140, vol. 125, Published in: Australia.

Rezvan Kiani et al., "Sources and Routes of Introduction of Eimeria Oocysts into Broiler Chick's Houses", "International Study of Poultry Science", 2007, pp. 925-927, vol. 6, No. 12, Published in: Ahvaz, Iran.

Kaio Kitazato et al., "Viral infectious disease and natural products with antiviral activity", "Drug Discoveries and Therapeutics", 2007, pp. 14-22, vol. 1, No. 1.

Hyun-A Lee et al., "Anticoccidial effects of Galla rhois extract on Eimeria tenella-infected chicken", "Laboratory Animal Research", 2012, pp. 193-197, vol. 28, No. 3.

T.Leela et al., "Studies of the Antibacterial Activity of Quercus Infectoria Galls", "International Conference on Bioscience, Biochemistry and Bioinformatics IPCBEE", 2011, pp. 410-414, vol. 5.

M.E.E. McCann Et A., "The Use of Mannan-Oligosaccharides and/or Tannin in Boiler Diets", "Internatioal Journal of Poultry Science", 2006, pp. 873-879, vol. 5, No. 9.

Abdul Lateef Molan et al., "Effect of pine bark (*Pinus radiata*) extracts on sporulation of", "Folia parasitologica", 2009, pp. 1-5, vol. 56.

V. Naidoo et al., "The value of plant extracts with antioxidant activity in attenuating coccidiosis in broiler chickens", "Veterinary Parasitology", 2008, pp. 214-219, vol. 153.

N.E. Nweze et al., "Anticoccidial effects of Ageratum conyzoides", "Journal of Ethnopharmacology", 2009, pp. 6-9, vol. 122.

Ojha et al., "Antioxidant Activity of Andrographis paniculata in Ischemic Myocardium of Rat", "Global Journal of Pharmacalogy", 2009, p. 154*157, vol. 3, No. 3.

Y. B. Rajeshwari et al., "Efficacy of DIAREX VET in Treating Rabbit Coccidiosis", "The Veterinarian", 2003, p. 12-13, vol. 27.

Simone Rochfort et al., "Plant bioactives for ruminant health and productivity", "Phytochemistry", 2008, pp. 299-322, vol. 69.

Nongyao Sawangjaroen et al., "The effects of extracts from anti-diarrheic Thai medicinal plants on the in vitro growth of the intestinal protozoa parasite: Blastocystis hominis", "Journal of Ethnopharmacology", 2005, pp. 67-72, vol. 98.

Nongyao Sawangjaroen et al., "Effects of Piper longum fruit, Piper sarmentosum root and Quercus infectoria nut gall on caecal amoebiasis in mice", "Journal of Ethnopharmacology", 2004, pp. 357-360, vol. 91.

Soon et al., "Ultrastructural Findings and Elemental Analysis of Quercus infectoria Oliv", "Annals of Microscopy", 2007, pp. 32-37, vol. 7.

Suryaprakash et al., "Pharmacological Review on Terminalia chebula", "International Journal of Research in Pharmaceutical and Biomedical Sciences", 2012, pp. 679-683, vol. 3, No. 2.

M. L. Wang et al., "Influence of Grape Seed Proanthocyanidin Extract in Broiler Chickens: Effect on Chicken Coccidiosis and Antioxidant Status", "Poultry Science", 2008, pp. 2273-2280, vol. 87.

R.B. Williams, "Intercurrent coccidiosis and necrotic enteritis of chickens: Rational, integrated disease management by maintenance of gut integrity", "Avian Pathology", Jun. 2005, pp. 159-180, vol. 34, No. 3.

G.F. Zhang et al., "Effects of ginger root (*Zingiber officinale*) processed to different particle sizes on growth performance, antioxidant status, and serum metabolites of broiler chickens", "Poultry Science", 2009, pp. 2159-2166, vol. 88, Published in: China.

McDougald et al., "Enhancement of Resitance to Coccidiosis and Necrotic Enteritis in Broiler Chickens by Dietary Muscandine Pomace", "Avian Diseases", 2008, pp. 646-651, vol. 52.

\* cited by examiner n =6, p<0.05

PLANT EXTRACTS HAVING ANTICOCCIDIAL ACTIVITY

This application is a divisional application of U.S. patent application Ser. No. 13/928,504 filed Jun. 27, 2013, which claims priority to U.S. Patent Application Ser. No. 61/664,795, filed Jun. 27, 2012 and Indian Application No. 177/DEL/2013, filed Jan. 23, 2013, both of which are hereby incorporated by reference.

BACKGROUND OF THE INVENTION

The present invention relates generally to the control of coccidiosis and, more specifically, to the application of plant parts, plant extracts and compounds to control coccidiosis in poultry and other animals.

Coccidiosis is a major disease in the poultry industry and according to a recent survey, it is estimated that the global impact is greater than $3 billion USD annually (worldpoultry.net/Broilers/Health/2009/9/In-ovo-vaccination-against-coccidiosis-WP006949W/—accessed Jun. 18, 2013). Coccidiosis is caused by a protozoan parasite, namely *Eimeria*, belonging to the phylum Apicomplexa, and the family Eimeriidae (Clare, R. A and Danforth, H. D (1989). Major histocompatibility complex control of immunity elicited by genetically engineered *Eimeria tenella* (Apicomplexa) antigen in chickens. *Infection and immunity*, 57 (3): 701-705). The parasite invades the gut cells and causes necrosis in the intestine which leads to malabsorption, diarrhea, morbidity, reduction of weight gain, poor feed conversion, and, in severe cases, mortality (Williams, R. B (2005). Intercurrent coccidiosis and necrotic enteritis of chickens: Rational, integrated disease management by maintenance of gut integrity. *Avian Pathology*, 34(3), 159-180). Seven different species of *Eimeria*, *E. acervulina*, *E. brunetti*, *E. maxima*, *E. mitis*, *E. necatrix*, *E. praecox*, and *E. tenella* are known to cause coccidiosis in poultry (Williams, 2005) and the species are highly host and site specific. *E. tenella* is one of the major species causing coccidiosis in poultry, and their site of infection is the caecum (Khazandi, M and Tivey, D (2010). Developing an in vitro method for *Eimeria tenella* attachment to its preferred and non-preferred intestinal sites. *Experimental Parasitology*, 125 (2), 137-140). Coccidiosis is currently controlled by medication, but the increasing emergence of drug-resistant strains of *Eimeria* requires the development of an alternative control strategy. Since plants are known to possess antiparasitic and anticoccidial activity due to the presence of phenolic compounds (Tipu, M. A., Akhtar, M. S., Anjum, M. I and Raja, M. L (2006), New dimension of medicinal plants as animal feed. *Pakistan vet. J.*, 26(3): 144-148), they could be potential sources of bioactive molecules against coccidiosis in poultry.

Others have attempted to use plant parts or plant extracts in treating coccidiosis. For example, McCann et al. tested the effect of Sweet Chestnut Wood tannins on the performance of broiler chicks vaccinated with a live coccidia vaccine (M. E. E. McCann, E. Newell, C. Preston and K. Forbes. The Use of Mannan-Oligosaccharides and/or Tannin in Broiler Diets. Intl. J. of Poultry Sci. 5 (9): 873-879, 2006). They reported that supplementation with mannan-oligosaccharides or tannins, either individually or in combination, did not reduce the impact of the coccidiosis.

Wang et al. teach the use of a grape seed proanthocyanidin extract on coccidiosis (Wang, et al. Influence of Grape Seed Proanthocyanidin Extract in Broiler Chickens: Effect on Chicken Coccidiosis and Antioxidant Status. Poultry Science. 87:2273-2280, 2008). They attributed activity to the anti-inflammatory and antioxidant properties of the proanthocyanidins, a condensed tannin rather than a hydrolysable tannin.

Naidoo et al. teach an in vivo study using four plants selected based on their antioxidant activity (Naidoo et al. The value of plant extracts with antioxidant activity in attenuating coccidiosis in broiler chickens. Veterinary Parasitology. 153:214-219; 2008). They observed that one of the plants (*Tulbaghia violacea*) reduced the *Eimeria* oocyst counts in the chicken excreta and they speculate that this effect could be due to the antioxidant compound S (methylthiomethyl) cysteine sulfoxide.

McDougald et al. describe the use of a muscadine pomace to enhance resistance to coccidiosis in broiler chickens (McDougald et al. Enhancement of Resistance to Coccidiosis and Necrotic Enteritis in Broiler Chickens by Dietary Muscadine Pomace. Avian Diseases. 52: 646-651; 2008). Muscadine pomace is a by-product of grapes used in wine production. They make no mention of efficacy of any specific compounds in the pomace. The proposed anticoccidial activity differs significantly from the activities proposed by Wang et al. and Naidoo et al.

SUMMARY OF THE INVENTION

The present invention consists of the identification and use of plant parts and plant extracts effective in the control of coccidiosis in animals, particularly in poultry. Specifically, plant parts and natural extracts of *Quercus infectoria*, *Rhus chinensis* gall nut, *Terminalia chebula* fruit have been found to control coccidiosis in poultry and, more specifically, coccidiosis caused by *Eimeria* spp. More specifically, plant parts or extracts containing efficacious amounts of compounds selected from the group consisting of gallic acid, gallotannins and hydrolys able tannins.

The plant parts and natural extracts of gall nuts of *Quercus infectoria*, *Rhus chinensis* and fruits of *Terminalia chebula* result in a reduction of lesion score, oocysts per gram of fecal matter and mortality. The plant parts/extract was also found to have a direct inhibitory effect on the sporozoites of *Eimeria*, as observed in the in vitro MTT assay. Compounds selected gallic acid, gallotannins and hydrolys able tannins were also found to reduce lesion score, oocysts per gram of fecal matter and mortality. The compounds were also found to have a direct inhibitory effect on the sporozoites of *Eimeria*, as observed in the in vitro MTT assay.

The present invention also consists of a method of controlling coccidiosis in poultry and other animals by administering a composition comprising plant parts or extracts of plants containing an efficacious amount of gall nuts of *Quercus infectoria*, *Rhus chinensis*, *Terminalia chebula* fruit and/or compounds such as gallic acid, gallotannins and hydrolysable tannins.

DESCRIPTION OF THE INVENTION

Figure 1:
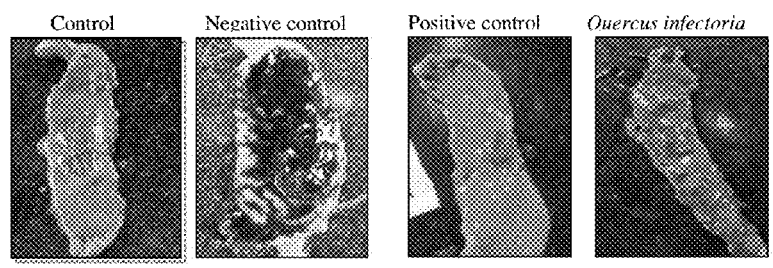
FIG. 1 is an image of caecal lesions of birds treated with *Quercus infectoria*

A preliminary in vivo evaluation of crude powder of *Q. infectoria* gall nuts (100-800 micron particle size, procured from Pooja Herbs, Mumbai, India) in controlling coccidiosis at 100 g/ton of feed dose gave some indication of promising results which urged further evaluation at higher dosage. A 35 day in vivo trial conducted in broiler birds challenged with oocysts of *Eimeria tenella* showed that *Q. infectoria* gall nuts reduced the lesion score to 0 and mortality to 0%, comparable to the positive control (0%), whereas the negative control showed a score of 4 and a mortality of 17%. The histopathological analysis of the caecum samples showed that the birds treated with *Q. infectoria* showed lesser area infected by the parasite, lower mononuclear infiltrations and hemorrhages of the caecum.

In general in this description, a plant part, extract or compounds is termed to be efficacious if it can result in statistically significant reduction in the lesion score, the oocysts shed in the excreta, (Oocyst Per Gram (OPG)) or the mortality of the birds as compared to the infected control which is untreated. Generally, administration of gallic acid and gallic acid containing formulations are described with formulations providing a dosage from 0.1 to 50 ppm, preferably from 2 to 20 ppm, and most preferably from 3 to 10 ppm through feed or water or an equivalent supplementation through other routes. The plants, plant parts and/or extracts described contain around a minimum of 0.1% of gallic acid.

The efficacy of *Q. infectoria* crude powder in controlling mixed infection of Eimeria in broiler birds was evaluated. The results showed that there was significant reduction in the lesion score for *E. tenella* and *E. acervulina* as compared to the infected control and even the positive control, Salinomycin. Whereas in case of *E. maxima*, a numerical reduction in the lesion score was observed as compared to the infected control and Salinomycin. The oocysts per gram of treated groups were significantly lower than the infected control and Salinomycin group, however, mortality was not observed in any of the treatment groups including the infected control. This proves the efficacy of *Q. infectoria* in controlling coccidiosis caused by other species of *Eimeria* also Further, to determine the mode of action of *Q. infectoria*, an in vitro method based on 3-(4,5-Dimethyl-2-thiazolyl)-2,5-diphenyl-2H-tetrazolium bromide (MTT) reduction assay was developed to evaluate the anti-sporozoite activity of plant extracts as a measure of the viability of the sporozoites. Studies with *Q. infectoria* gall nut on the sporozoites of *Eimeria tenella* showed significant reduction in the viability of sporozoites compared to the sporozoite control. A dose dependent efficacy was observed in studies conducted with different dosages of *Q. infectoria* and the results were validated by conducting experiments several times independently. Hence, direct anti-sporozoite activity of *Q. infectoria* could be one of the modes of actions which attributes to the efficacy of the extract in controlling in coccidiosis in vivo.

Similarly, to determine the mode of action of *Q. infectoria* in controlling *Eimeria* in a host cell line, an in vitro assay was developed based on a co-culture of host cells and *Eimeria* parasites. Cells and parasite are combined in an assay with a positive control and different test products. The invasion and proliferation of the *Eimeria* parasites is measured by detecting *Eimeria* DNA using real-time PCR. For this, specific primers were selected and PCR conditions were optimised. The positive control and potential anticoccidial compounds are added to the in vitro assay in three different ways:

The products are combined with *Eimeria* sporozoites and added to the host cells.

The products are added to the sporozoites for a specific time, then removed and afterwards the sporozoites are added to the host cells.

The products are added to the host cells for a specific time, then removed and afterwards the sporozoites are added to the host cells.

The effect of *Quercus infectoria* was evaluated in the in vitro assay.

Example 1

Efficacy of *Quercus infectoria* in controlling caecal coccidiosis

Experimental facility and study design. The screening trial was conducted at a poultry farm facility located in Gummidipundi, India. Straight run commercial hybrid broiler chickens, *Gallus domesticus* (Var. Vencobb 400) were used for the study. Day old male chicks were procured, weighed individually, wing banded, and randomly segregated into groups. The experimental design is detailed in Table 1.

TABLE 1

Study design.

| Category | Trial Parameter |
| --- | --- |
| Rearing type | Cages |
| Age of birds at the start of the trial | 1 day old |
| Total no of Birds | 56 |
| Number of groups | 8 |
| No of birds/groups | 7 |
| Duration of the trial | 35 days |

Farm management. Good farm managing practices were followed during the trial. The entire farm and the equipment used for the study were cleaned and disinfected before the arrival of the chicks. The birds were housed in cages organized on concrete flooring and a tray was provided at the bottom of the cages to facilitate collection of fecal samples. The temperature and humidity of the farm was monitored continuously.

Vaccination schedule. The birds were vaccinated for Newcastle Disease Virus (NDV) and Infectious Bursal Disease (IBD).

Feed formulation. A corn soya based mash diet was formulated. The feed ingredients were procured from Ponni feeds, Tamil Nadu, India. The mash feed was fed ad libitum to the birds throughout the study period. Three feed formulations were prepared according to the phases of the life of the bird; Prestarter (Day 1-10), Starter (Day 11-20), and Finisher feed (Day 21-42). No antimicrobials and supplements were used in the feed formulation.

Details of treatment groups. Groups and the treatments are shown in Table 2. The treated birds were fed with plant extract incorporated in the feed from day 1 (Table 2). The crude powders of *Q. infectoria* gall nut were procured from Pooja herbs, Mumbai, India.

TABLE 2

Details of treatment groups and feed.

| Groups | Treatments |
| --- | --- |
| Control 1 (uninfected control) | Normal feed |
| Control 2 (Negative infected Control) | Coccidiosis induction + Normal feed |
| Control 3 (Positive Control) | Coccidiosis induction + Feed with Coxistac* at 1000 g/ton |
| Treatment | Coccidiosis induction + Feed with *Q. infectoria* at 100 g/ton |

*Coxistac is a product from Pfizer containing Salinomycin at 12% concentration. Hence, addition of Coxistac at the mentioned dose of 500 g/ton of feed will enable delivery of Salinomycin at 60 ppm levels in the feed which is the recommended preventive dose for broilers. The dose in this experiment was double the recommended concentration.

Induction of coccidiosis. Sporulated oocysts of *E. tenella* (Houghton strain [Chapman, H. D. and Shirley, M. W. 2003. The Houghton strain of *Eimeria tenella*: A review of the type strain selected from genome sequencing. *Avian Pathol.*, 32: 115-127]-propagated) were orally administered to each bird on day 14, 15 and 16 of age through oral gavage at a dose of $1 \times 10^5$ oocysts/bird/day. Feeding was stopped on the day of inoculation, for 2 h before and 2 h after inoculation.

Parameters analyzed. The parameters that were chosen for analyses were the indices of pathogenesis namely excreta appearance, mortality, lesion scoring of the caecum for coccidiosis, and oocysts per gram (OPG) of excreta. The methods are detailed below.

Examination of excreta. The excreta of the birds were monitored daily from the day 1 post infection to day 10 for their consistency, presence of blood, mucus, undigested feed, and orange color. Scoring of the excreta was carried out based on the severity of blood shedding.

Mortality. The mortality of the birds was recorded on a daily basis and post mortem was carried out to confirm the cause of death.

Lesion scoring of the caecum. On day 5 and 7 post infection, 2 birds from each of the groups were sacrificed by cervical dislocation and the intestine was cut open. The caeca of the birds were scored for coccidiosis lesions. The scoring was done based on the severity of the lesions in the caecum and the presence of blood (Johnson, J. K., and W. M. Reid. (1970). Anticoccidial drugs: lesion scoring techniques in battery and floor-pen experiments with chickens. Experimental Parasitology 28:30-36). The score for caecal coccidiosis was a scale of 0-4.

OPG of excreta. Triplicate samples of the excreta of the birds were collected randomly from the tray kept below the cages and the oocyst per gram was evaluated.

Results

Indices of pathogenesis. The observations on the excreta of the birds showed that the blood shedding in the infected groups started by day 4 post infection and the severity peaked on the day 5. The results of the scoring of the excreta are given in Table 3. Day 7 post infection the excreta were found to be normal with no blood. The positive control (C3, Table 3) on day 5 had a score of 3 as compared to the negative control (C2, Table 3) of 4. Birds treated with *Q. infectoria* had a lower score of 2 and were better than the positive control.

TABLE 3

Scoring of excreta on day 5 post infection.

| Treatments | Score | Description |
| --- | --- | --- |
| C1-uninfected control | 0 | Excreta normal consistency |
| C2-Negative infected control | 4 | Presence of heavy raw blood |

TABLE 3-continued

Scoring of excreta on day 5 post infection.

| Treatments | Score | Description |
|---|---|---|
| C3-Positive Control | 3 | Excreta with blood +++ |
| T-Q.infectoria at 100 g/ton | 2 | Excreta with blood ++ |

+-denotes the severity of blood loss and amount of blood in the excreta.

Lesion scoring of the caecum. Lesion scoring of the caeca on day 5 and 7 post infection indicated that the lesions were severe on day 5, and the birds started recovering on day 7 post infection which was indicated by the formation of a caecal plug. This followed the normal pattern of infection enabling the removal of oocysts from the caeca. The results of the lesion score showed that the positive control (Salinomycin control did not show any difference in the score as compared to the negative control due to inexplicable reasons. The treatment with Q. infectoria reduced the lesion score as compared to the negative control (Table 4). The reduced lesion score correlated with reduced excreta score and absence of mortality.

TABLE 4

Lesion score of the caeca on day 5 post infection

| Treatments | Lesion Score |
|---|---|
| C1-uninfected control | 0 |
| C2-Negative infected control | 3 |
| C3-Positive Control | 3 |
| T-Q. infectoria at 100 g/ton | 2.5 |

OPG of excreta of the birds on day 7 post infection. The counts of OPG of excreta of the birds on day 7 post infection are shown in Table 5. Unexpectedly, the anticoccidial Salinomycin treated birds (C3, Table 5) did not show any indication of reduction of oocysts as compared to the C2 (Table 5). The values presented are an average of three replicates.

TABLE 5

Oocysts per gram of excreta on day 7 post infection

| Treatments | Average Oocysts Per Gram Excreta | CV |
|---|---|---|
| C2-Negative infected control | 2.5E+05 | 1.23 |
| C3-Positive Control | 4.0E+05 | 0.68 |
| T-Q.infectoria at 100 g/ton | 3.5E+05 | 1.36 |

Mortality. The rate of mortality was 17% in control 2 (negative infected control). There was no mortality in other groups. The lesion score and OPG data of the positive control did not show any difference from that of the negative control.

Although the positive control did not perform well in this trial, the lesion scores of birds treated with plant extracts of Q. infectoria were lower than the negative infected control which indicates that they could be candidates for further investigation. However, they showed no reduction in the OPG.

Example 2

Efficacy of Quercus infectoria in controlling caecal coccidiosis

A 35 day in vivo challenge trial was conducted in broiler birds challenged with Eimeria tenella The treatment groups included, 1) control, uninfected normal birds; 2) negative control, birds infected with E. tenella and fed normal diet without any anticoccidial compounds; 3) positive control, birds infected and fed diet containing Coxistac (anticoccidial agent, Salinomycin) at the recommended dose of 500 g/ton and 4) treatment group including infected birds administered diet containing Q. infectoria gall nut at 500 g/ton dose. No mortality was observed in the positive control group and treatment group supplemented with crude powder of gall nuts of Quercus infectoria. The caecal lesions indicated that the negative control birds were highly infected with an average score of 4 whereas the positive control had score of 0. Birds treated with Quercus infectoria showed results similar to the positive control (0). Q. infectoria showed reduction in the OPG counts comparable to the positive control. The histopathological analysis of the caecum samples showed that the birds treated with Q. infectoria had lesser area affected by Eimeria, no hemorrhages and minimal mononuclear infiltrations up to the mucosa.

The second in vivo experiment involved the following treatment groups.

TABLE 6

Description of treatment groups

| Groups | Treatments |
|---|---|
| Control 1 (C1) | Uninfected control-Normal feed without anticoccidial |
| Control 2 (C2) | Negative control-Coccidiosis induction + Normal feed without anticoccidial |
| Control 3 (C3) | Positive Control-Coccidiosis induction + Normal feed with Coxistac 12% @ 500 g/ton* |
| Treatment (T) | Coccidiosis induction + Normal feed w Q. infectoria |

*Coxistac is a product from Pfizer containing Salinomycin at 12% concentration. Hence, addition of Coxistac at the mentioned dose of 500 g/ton of feed will enable delivery of Salinomycin at 60 ppm levels in the feed which is the recommended preventive dose for broilers.

Results

Caecal lesions on day 5 post infection. The lesion scoring for caecal coccidiosis was carried out on day 5 post infection based on the criteria of scoring as before. The results of the scoring showed that the positive control completely alleviated the effects of caecal coccidiosis as compared to the negative infected control. Q. infectoria treated birds showed no lesions in the caecum and was comparable to the positive control and uninfected control C1 (Table 7, FIG. 1).

TABLE 7

Lesion scoring on day 5 post infection.

| Treatments | Lesion Score |
|---|---|
| C1-Uninfected control | $0^e$ |
| C2-Negative infected control | $4^a$ |
| C3-Positive Control | $0^e$ |
| T-Q. infectoria | $0^e$ |

Columns with different superscripts are statistically significant (p < 0.05).

Figure 2:
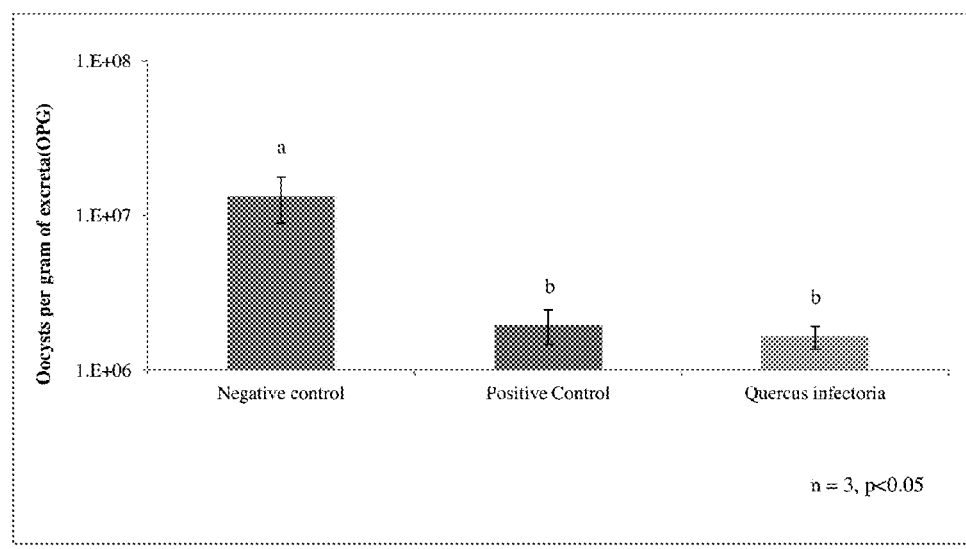
FIG. 2 is a chart of the oocysts per gram (OPG) of excreta of birds treated with *Quercus infectoria* on day 7 post infection; columns with different superscripts are statistically significant ($p<0.05$).

Oocyst counts in excreta. The OPG of excreta was estimated on day 7 post infection to evaluate the shedding of oocysts. The results of the study showed that the positive control, Q. infectoria had significantly lower counts of oocysts in the excreta as compared to the infected negative control (p<0.05). Q. infectoria treatment was equally effective as the positive control (FIG. 2). This correlates with the results of the lesion score.

Mortality. The rate of mortality was recorded during the experiment, and the data are given in Table 8. As expected, there was no mortality in the uninfected control group (C1)

and the positive control group (C3). *Q. infectoria* supplemented group showed no mortality.

TABLE 8

Rate of mortality during the trial period

| Treatment Groups | Rate of mortality (%) |
|---|---|
| C1-Uninfected control | 0 |
| C2-Negative infected control | 33.33 |
| C3-Positive Control | 0 |
| T-*Q. infectoria* | 0 |

Histopathological analysis of caecum samples. *Q. infectoria* showed positive reductions in all parameters tested such as lesion score, OPG and rate of mortality and the data were comparable to the positive control, Salinomycin. Hence, histopathological analysis of the caecum samples of birds from this group was carried out in comparison to the uninfected control (C1), negative control (C2) and positive control (C3). The severity and distribution of the lesions in the caecum were based on the grading provided in Table 9.

TABLE 9

Severity and distribution of lesions in the caecum of different groups

| Histopathology | Uninfected control | Negative control | Positive control | *Quercus infectoria* |
|---|---|---|---|---|
| Mononuclear cell infiltration-mucosa | 0 | 3 | 2 | 1 |
| Mononuclear cell infiltration-submucosa | 0 | 2 | 3 | 0 |
| Mononuclear cell infiltration-muscular layer | 0 | 2 | 0 | 0 |
| Hemorrhages | 0 | 2 | 1 | 0 |
| Necrosis-Villi | 0 | 1 | 1 | 1 |
| Distribution of stages of *Eimeria* | 0 | 3 | 1 | 1 |

TABLE 10

Histopathological findings of the tissues of caecum of birds

| Groups | Histopathological findings |
|---|---|
| Uninfected control C1 | Cecum within normal histological limits. |
| Negative control C2 | Cecum showed moderate load of different Eimerial stages (oocyst, schizont and merozoite) along with mild mucosal hemorrhages and mild to moderate mononuclear cell infiltration in mucosal, submucosal and muscular layers. |
| Positive control C3 | Cecum showed minimal load of different Eimerial stages with schizonts and merozoites contributing the major load. Minimal mucosal hemorrhages and necrosis was evident microscopically. Mild to moderate mononuclear cell infiltration in mucosal and submucosal layers was seen. |
| *Q. infectoria* T | Cecum showed minimal load of different Eimerial stages with oocyst contributing the major load. Minimal mucosal necrosis and mononuclear cell infiltration in mucosal layers was evident. |

Figure 3:
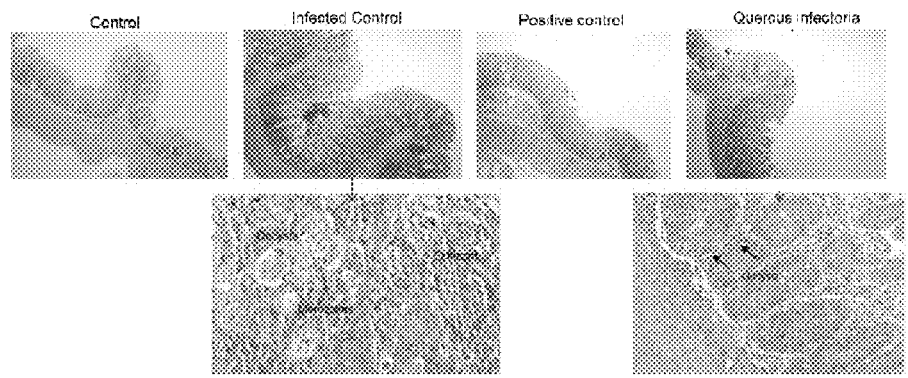
FIG. 3 is microphotographic images of the H and E stained sections of caecum of birds treated with *Quercus infectoria*.

Histopathological results showed that the birds treated with *Q. infectoria* had fewer regions of the caecum infected with *E. tenella*, and the mononuclear infiltration was restricted only to the mucosa with a score of 1 indicating mild infiltration (FIG. 3). The submucosa and muscular layers were free from infiltration (Table 10). In the negative control, mononuclear infiltration was observed in the mucosa, submucosa and even the muscular layer. There were no hemorrhages in the caecum of birds treated with *Q. infectoria* as compared to that of the negative control (2). This indicates that the caecum of birds treated with *Q. infectoria* was less infected than the positive control.

The in vivo screening of plant extracts revealed that *Quercus infectoria* is a potent candidate in controlling caecal coccidiosis in broiler birds caused by *E. tenella*. The efficacy of the extract was found to be on par with that of the positive control in terms of reducing lesion score, OPG and rate of mortality.

Example 3

Efficacy of water extracts of *Quercus infectoria* in controlling mixed infection of coccidiosis Efficacy of *Q. infectoria* crude powder in controlling mixed infection of coccidiosis in broiler birds was evaluated. A 35 day in vivo trial was conducted wherein the birds were challenged with field strains of mixed culture of oocysts of the species *E. tenella, E. acervulina* and *E. maxima*. The mixed culture of oocysts was provided by Department of parasitology, Tamil Nadu Veterinary Research Institute, Namakkal, India. The oocysts culture was a mixture of *E. tenella, E. acervulina* and *E. maxima* isolated from feces of birds with clinical coccidiosis infection. Virulence of the oocysts obtained was evaluated in broiler birds and the dosage of the oocysts was finalized to be $5 \times 10^5$ based on the concentration that yields a lesion score of 3 and above for all the tested oocysts, *E. tenella, E. maxima* and *E. acervulina*.

a. The screening trial was conducted at Kemin's in-house R&D poultry farm facility located in Gummidipundi, India. Straight run commercial hybrid broiler chickens, *Gallus domesticus* (Var. Vencobb 400) were used for the study. Day old male chicks were procured, weighed individually, wing banded, and randomly segregated into groups. The experimental design is detailed in Table 11. Good farm managing practices and vaccination schedule were followed during the $3^{rd}$ in vivo trial as mentioned in example 1.

TABLE 11

Study design

| Category | Trial Parameter |
|---|---|
| Duration of the trial | 35 days |
| Breed | Cobb 400 |
| Rearing type | Cages |
| Age of birds at the start of the trial | 1 day old |
| Total no of Birds | 315 |
| Number of groups | 21 |
| No of birds/groups | 15 (male) |

The birds were vaccinated for Newcastle Disease Virus (NDV) and Infectious Bursal Disease (IBD). A corn soya based mash diet was used for the study. The birds were fed with the extract of *Q. infectoria* gall nut incorporated in the feed from day 1. The treatment groups are given in Table 12.

TABLE 12

Details of treatment groups for the trial

| Groups | Diet |
|---|---|
| Control 1 | No infection + normal feed |
| Control 2 | Coccidiosis induction + normal feed without anticoccidial |

TABLE 12-continued

Details of treatment groups for the trial

| Groups | Diet |
|---|---|
| Control 3 | Coccidiosis induction + Normal feed with Coxistac 12% premix (500 g/ton) |
| Treatment | Coccidiosis induction + Normal feed with *Q. infectoria* water extract at 100 g/ton |

Extracts of gall nut of *Q. infectoria* were prepared by mixing the crude powder (100-800 micron particle size) in distilled water at the ratio of 1:2, then extracting at 80 to 90° C. for one and half hour with agitation. The extract was filtered and again the residue was extracted in water in a similar manner. This was repeated for about 2 more times and the total liquid extract was freeze dried.

Figure 4:
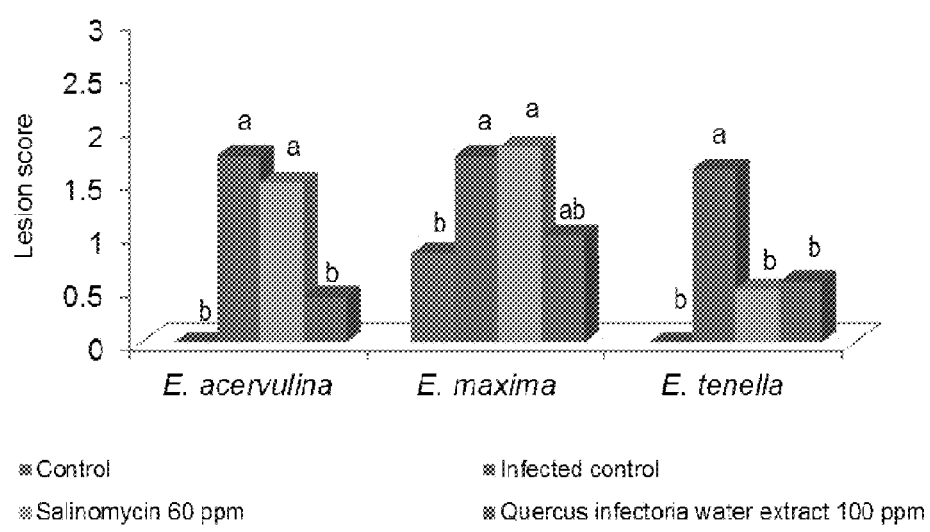
FIG. 4 is a chart of the lesion score for *E. acervulina*, *E. maxima* and *E. tenella* for the birds treated with *Q. infectoria* water extract on day 5 post infection; columns with different superscripts are statistically significant (p<0.05).
Figure 5:
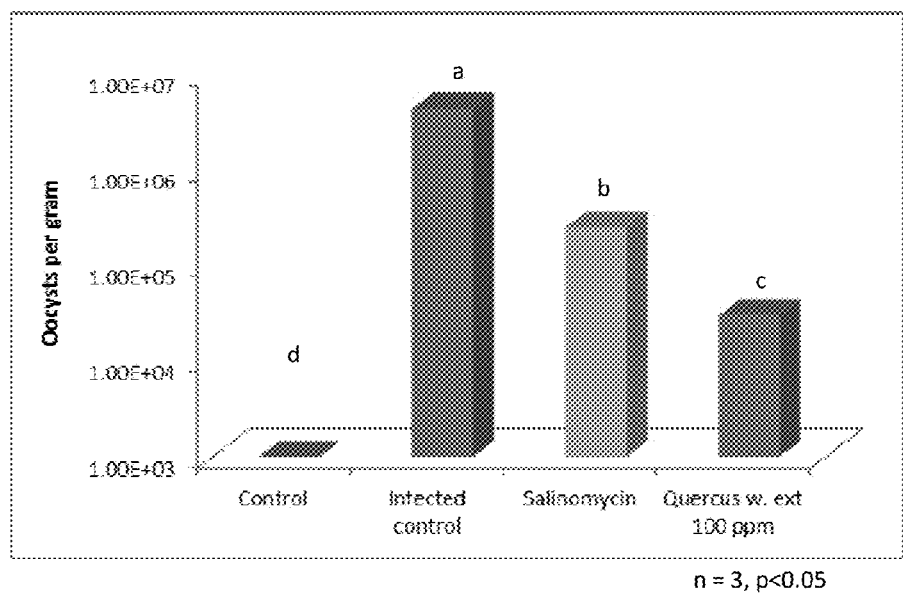
FIG. 5 is a chart of the oocysts per gram (OPG) of excreta of birds treated with *Q. infectoria* water extract on day 7 post infection; columns with different superscripts are statistically significant (p<0.05).

The results showed that there was significant reduction in the lesion score for *E. tenella* and *E. acervulina* as compared to the infected control and even the positive control, Salinomycin. Whereas, in case of *E. maxima*, a numerical reduction in the lesion score was observed as compared to the infected control and Salinomycin (FIG. 4). The oocysts per gram of treated groups were significantly lower than the infected control and Salinomycin group (FIG. 5), however, mortality was not observed in any of the treatment groups including the infected control. This proves the efficacy of *Q. infectoria* in controlling coccidiosis caused by other species of *Eimeria* also.

Example 4

In Vitro anti-sporozoite activity of *Q. infectoria* by MTT Assay

Further, an in vitro method based on 3-(4,5-Dimethyl-2-thiazolyl)-2,5-diphenyl-2H-tetrazolium bromide (MTT) reduction assay was developed to evaluate the anti-sporozoite activity of plant extracts as a measure of the viability of the sporozoites. The optimized method included the preparation, sterilization and purification of sporozoites, followed by incubation of sporozoite suspension (minimum of $10^5$ cells/ml) with required concentration of plant extract. The plant samples were prepared by mixing crude powder into a known volume of distilled water to achieve the specific ppm, vortexed for 2 min and filtered through a 0.2μ syringe filter. Following 24 h of incubation with the plant extracts, the sporozoites were thoroughly washed and then MTT assay was performed. MTT-PMS solution (0.2 millimolar each) is incubated with the sporozoite suspension (at 1:10 ratio) for 2 h at 41° C. After incubation, the contents are centrifuged at 800 g for 5 min and the supernatant is carefully removed. The purple dye formazan is dissolved in 200 ul DMSO and the absorbance is measured at 530 nm against a reference wavelength of 630 nm.

Figure 6:
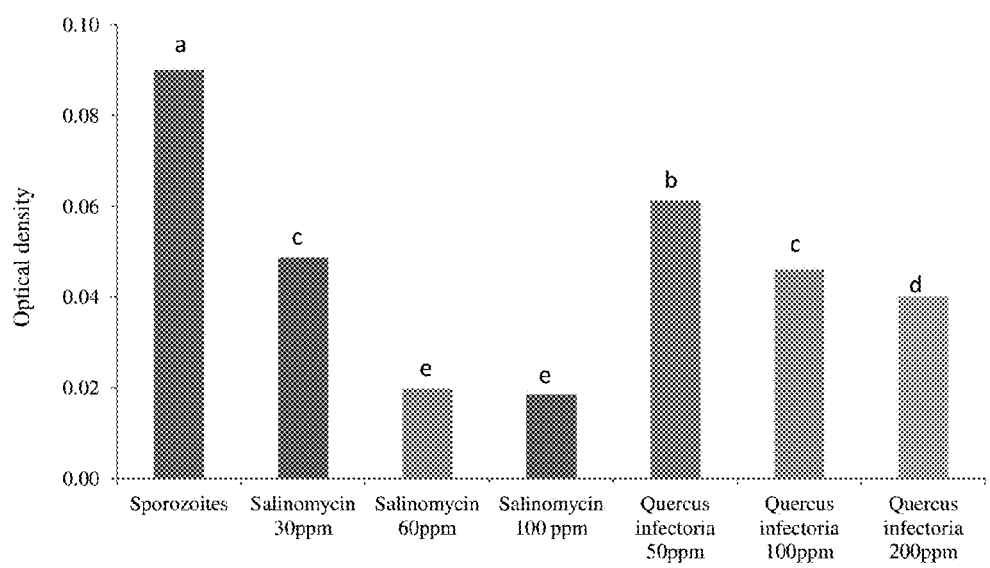
FIG. 6 is a chart of the MTT assay carried out for the evaluation of *Q. infectoria* at various dosage levels along with a coccidiostat (Salinomycin) as positive control; columns with different superscripts are statistically significant (p<0.05).

MTT assay was carried out for the evaluation of *Q. infectoria* at various dosage levels along with Coccidiostac (Salinomycin) as positive control (FIG. 6). There was a dose dependent reduction in the viability of sporozoites in the *Q. infectoria* treated samples as compared to the control.

Example 5

In vitro effect of *Q. infectoria* on *Eimeria tenella* sporozoite invasion and proliferation in host cells An experiment was conducted to evaluate the in vitro effect of *Q. infectoria* on *Eimeria tenella* sporozoite invasion and proliferation of host cells.

Sporozoites were obtained from sporulated oocysts after glass bead grinding and enzymatic excystation. As host cells, Madin-Darby Bovine Kidney (MDBK) cells, were selected. Sporozoites and *Quercus infectoria* at 50 and 100 ppm were added to MDBK host cells for four hours. Afterwards, the medium was removed, cells were washed and fresh medium was added. After 4 (T4), 24 (T24), 48 (T48) and 72 (T72) hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 μg/ml solution of Salinomycin.

Figure 7:
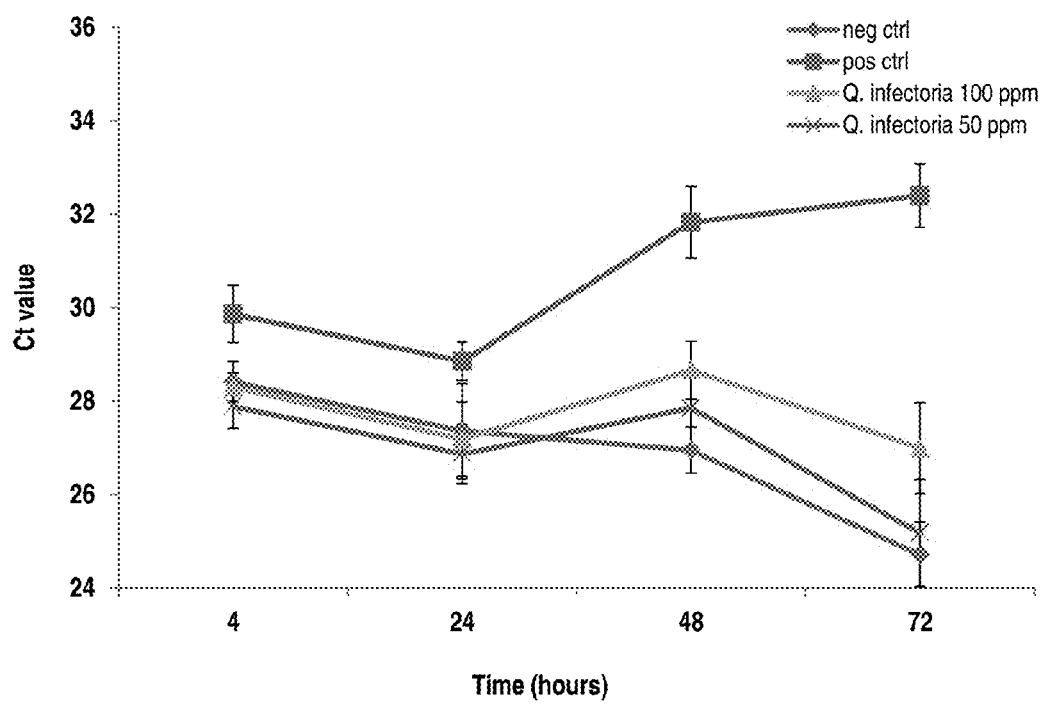
FIG. 7 is a chart of PCR results after invasion of MDBK host cells with sporozoites and different concentrations of *Q. infectoria*.

At the different collection time points, DNA was extracted from the infected MDBK cells. Real-time PCR to detect *Eimeria* DNA was performed on the samples for the different time points and different treatments. The PCR results are presented in FIG. 7.

Real-time PCR analyses

Differences in Ct values were calculated for each time point versus T4 within one treatment (ΔCt). Fold changes were calculated for each time point versus T4 using the following equation:

$$\text{Fold change} = 2^{-\Delta Ct}$$

Figure 8:
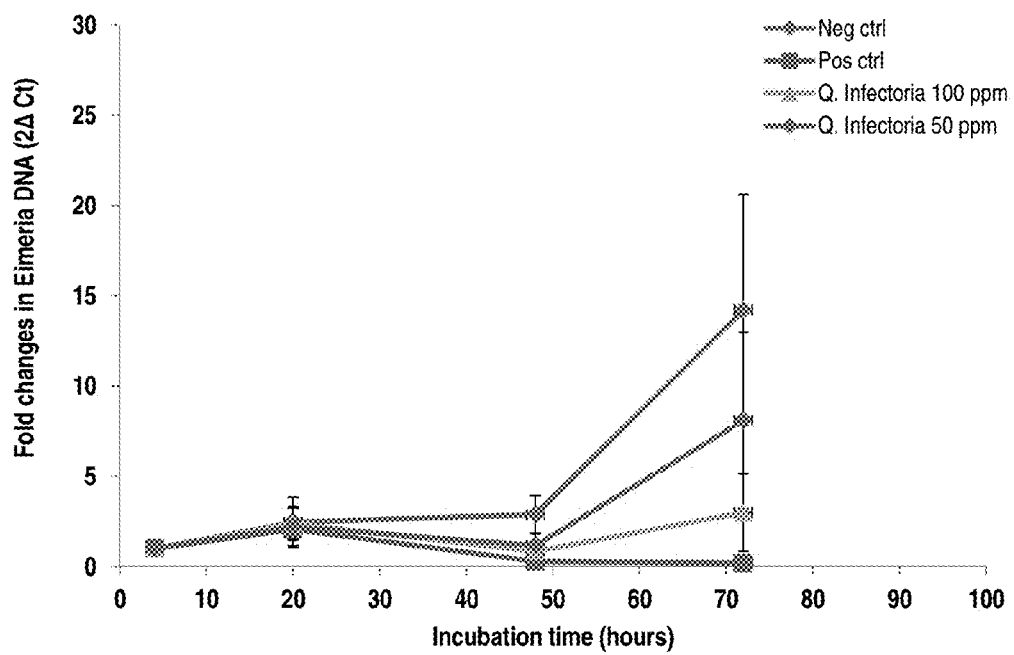
FIG. 8 is a chart of fold changes in *Eimeria* DNA for different time points versus T4 within one treatment.

These results are presented in FIG. 8.

The negative control shows a clear *Eimeria* proliferation since there is a 15 fold increase in *Eimeria* DNA at 72 hours versus the start at 4 hours. The positive control was able to inhibit the proliferation completely. Also for the *Q. infectoria* treatments, a clear inhibition of the proliferation was observed versus the start of 4 hours, in a dose dependent manner.

Example 6

In vitro effect of *Q. infectoria* on *Eimeria tenella* sporozoite invasion and proliferation in host cells An experiment was conducted to evaluate the in vitro effect of *Q. infectoria* on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 50, 100 and 250 ppm of *Quercus infectoria* for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 μg/ml solution of Salinomycin.

Figure 9:
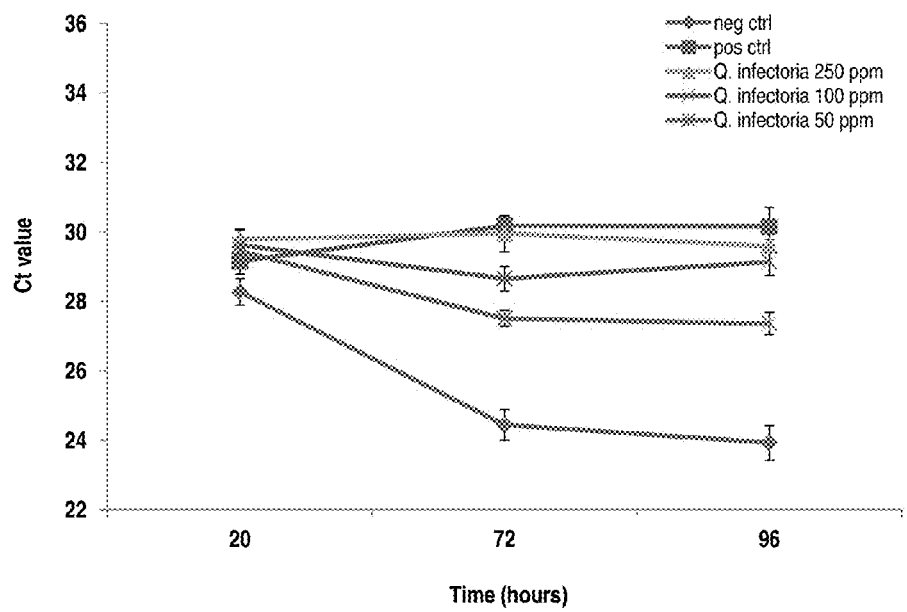
FIG. 9 is a chart of PCR results after invasion of MDBK host cells with sporozoites, pre-treated with different concentrations of *Q. infectoria*.

At the different collection time points, DNA was extracted from the MDBK cells. Real-time PCR to detect *Eimeria tenella* DNA was performed on the samples for the different time points and different treatments. The PCR results are presented in FIG. 9.

Real-time PCR analyses

Differences in Ct values were calculated for each time point versus T20 within one treatment (ΔCt). Fold changes were calculated for each time point versus T20 using the following equation:

$$\text{Fold change} = 2^{-\Delta Ct}$$

Figure 10:
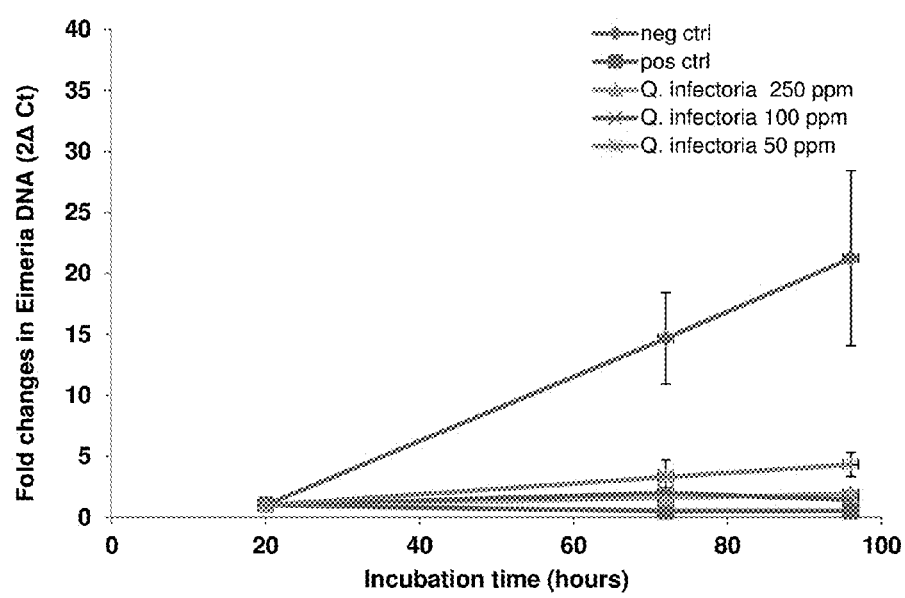
FIG. 10 is a chart of fold changes in *Eimeria* DNA for different time points versus T20 within one treatment.

These results for *Q. infectoria* are presented in FIG. 10.

The negative control shows a clear *Eimeria* proliferation since there is a 20 fold increase in *Eimeria* DNA at 96 hours versus the start at 20 hours. The positive control was able to inhibit the proliferation completely. Also the different dosages of *Q. infectoria* all inhibited the *Eimeria* proliferation. There was a slightly lower effect visible for 50 ppm *Q. infectoria*. But this is negligible in comparison to the increase in the negative control.

Example 7

Identification of Active Ingredients of *Q. infectoria*

Figure 11:
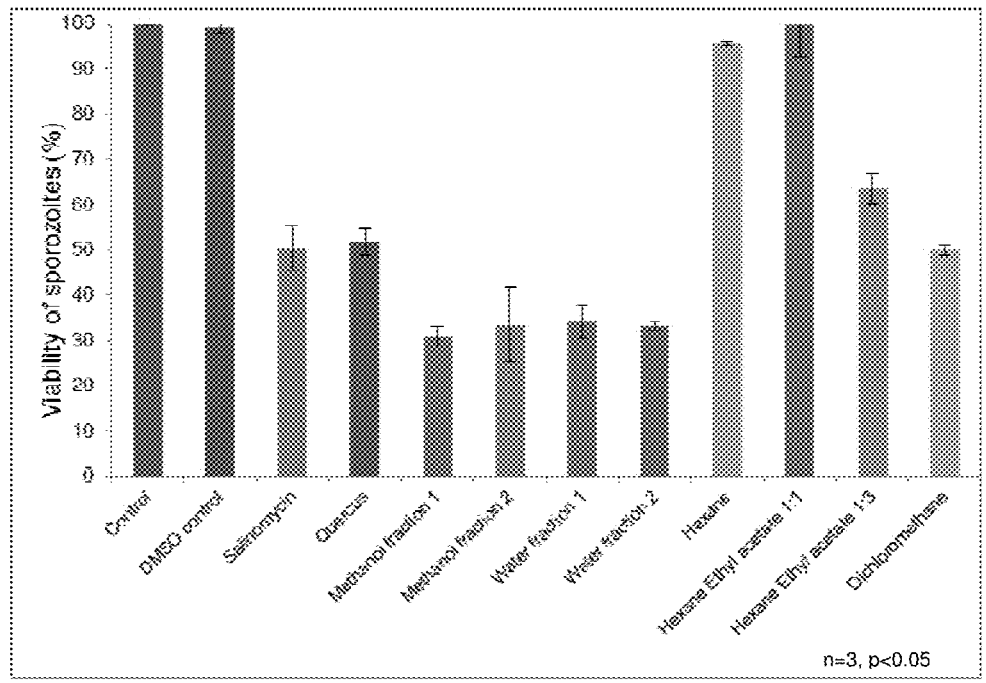
FIG. 11 is a chart of the anti-sporozoite activity of the different fractions of *Q. infectoria*; columns with different superscripts are statistically significant (p<0.05).

Further to this, Bioassay Guided Fractionation assay (BGFA) of *Q. infectoria* gall nuts was carried out using the modified MTT reduction assay as the bioassay as we had identified that the crude extract possess anti-sporozoite activity and this could be one of the mode of action by which it is able to control coccidiosis. *Q. infectoria* gall nut crude powder was fractionated using different solvent by column chromatography. The sample from each of the fractions was evaluated for their anti-sporozoite activity. Methanol and water fractions of *Q. infectoria* showed better reduction in the viability of sporozoites as compared to the other fractions and were comparable to the Salinomycin control (FIG. 11).

Figure 12:
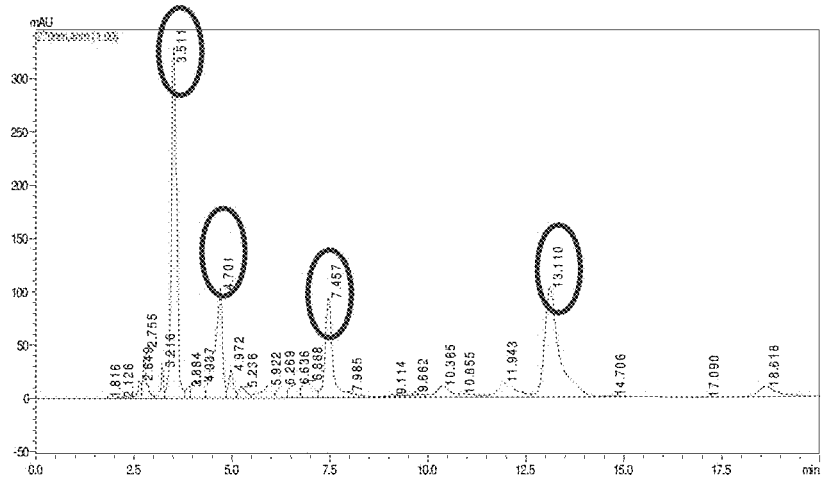
FIG. 12 is a High Performance Liquid Chromatogram (HPLC) chromatogram of water fraction of *Q. infectoria*.

Phytochemical analyses of the active fractions were carried out by High Performance Liquid Chromatography (HPLC) to identify the active ingredient/s responsible for the anti-sporozoite activity. Four major peaks were observed in the HPLC chromatogram of both methanol and water fractions, with one peak corresponding to the retention time of a gallic acid standard (FIG. 12). *Q. infectoria* gall nut are known to possess 60 to 70% hydrolysable tannins which can hydrolyse to release gallic acid in addition to about 7% free gallic acid present in it.

Figure 13:
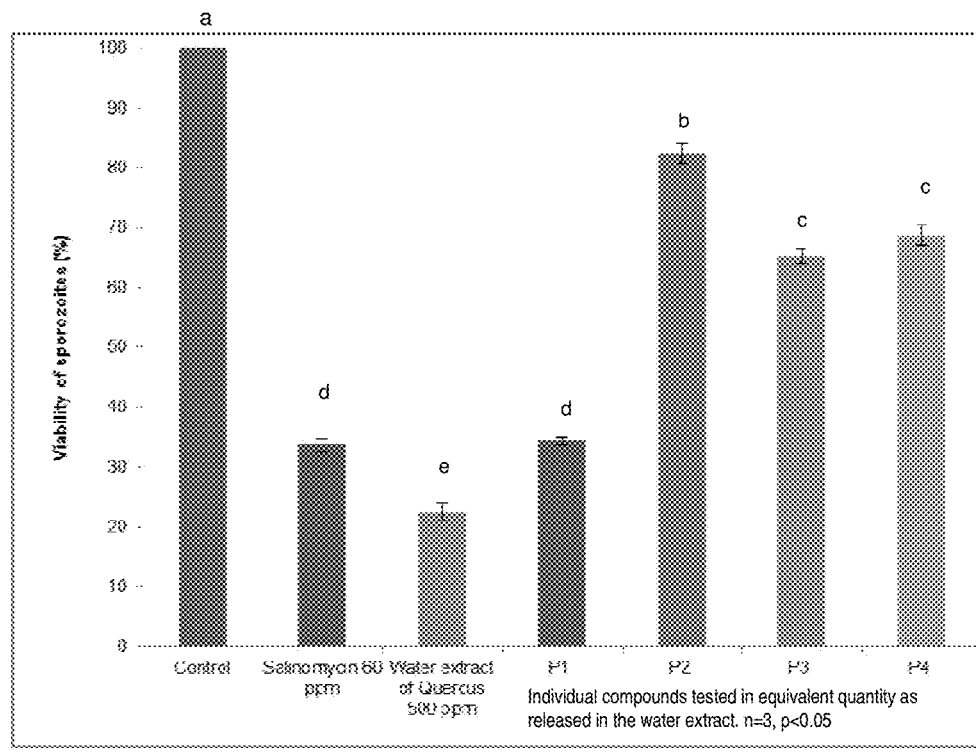
FIG. 13 is a chart of the anti-sporozoite activity of the four major peaks of *Q. infectoria*; columns with different superscripts are statistically significant (p<0.05).

These four compounds were separated by semi-preparative HPLC and anti-sporozoite activity was evaluated in comparison to the crude powder in equivalent concentrations. The anti-sporozoite activity of the compounds showed that compound of peak 1 had the best anti-sporozoite activity. The other compounds showed minimal activity against the sporozoites. However, the crude powder showed better activity than the peak 1 indicating synergistic activity of the compounds from the extract (FIG. 13).

Figure 14:
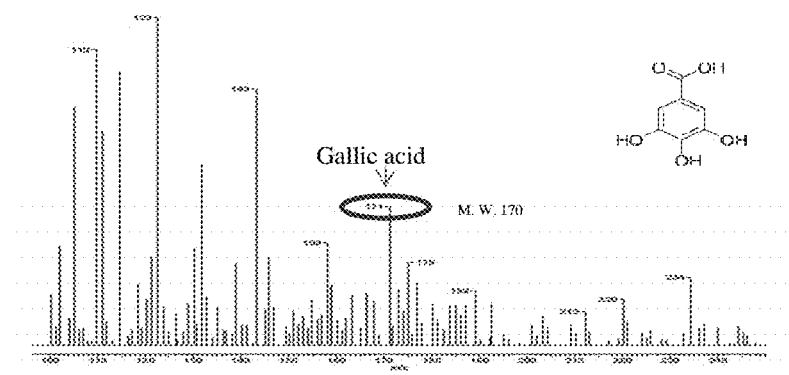
FIG. 14 is the LC/MS/MS chromatogram of peak 1 of *Q. infectoria*.

LC/MS/MS analysis of the different peaks of the HPLC chromatogram confirmed that peak 1 was gallic acid (FIG. 14) and the other peaks were high molecular weight compounds which could be degraded products of hydrolys able tannins. It was hypothesized that these compounds can further breakdown to release gallic acid.

Figure 15:
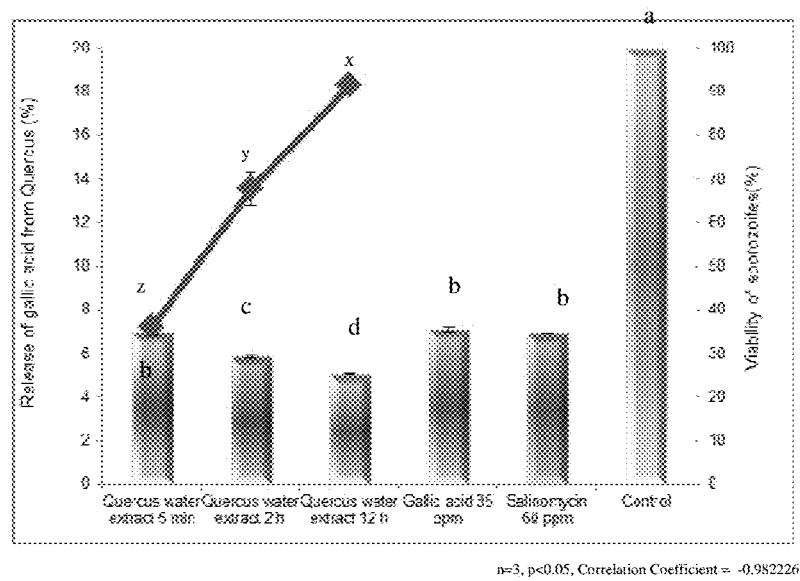
FIG. 15 is a chart depicting the correlation between the concentration of gallic acid and the anti-sporozoite activity of *Q. infectoria*; columns with different superscripts are statistically significant (p<0.05).

Further, to arrive at the correlation between gallic acid % and anti-sporozoite activity, *Q. infectoria* was extracted in water for 5 min, 2 and 12 h and their anti-sporozoite activity was evaluated. The study showed that there was a clear correlation (correlation coefficient=−0.982226) between the concentration of gallic acid and anti-sporozoite activity (FIG. 15). These results indicate that gallic acid is the active ingredient responsible for the anti-sporozoite activity of *Q. infectoria*.

Example 8

In Vitro protective effect of Gallic Acid

An experiment was conducted to evaluate the in vitro protective effect of gallic acid monohydrate on host cells challenged with *Eimeria tenella* sporozoites.

Sporozoites were obtained from sporulated oocysts after glass bead grinding and enzymatic excystation. As host cells, Madin-Darby Bovine Kidney (MDBK) cells, were selected. MDBK cells were incubated with 10 ppm gallic acid for seven hours. Afterwards the medium was removed and a sporozoite suspension was added to the MDBK cells for 20 hours. After incubation, the medium was removed, cells were washed and fresh medium was added. After 20, 72 and 96 hours the medium and the MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 16:
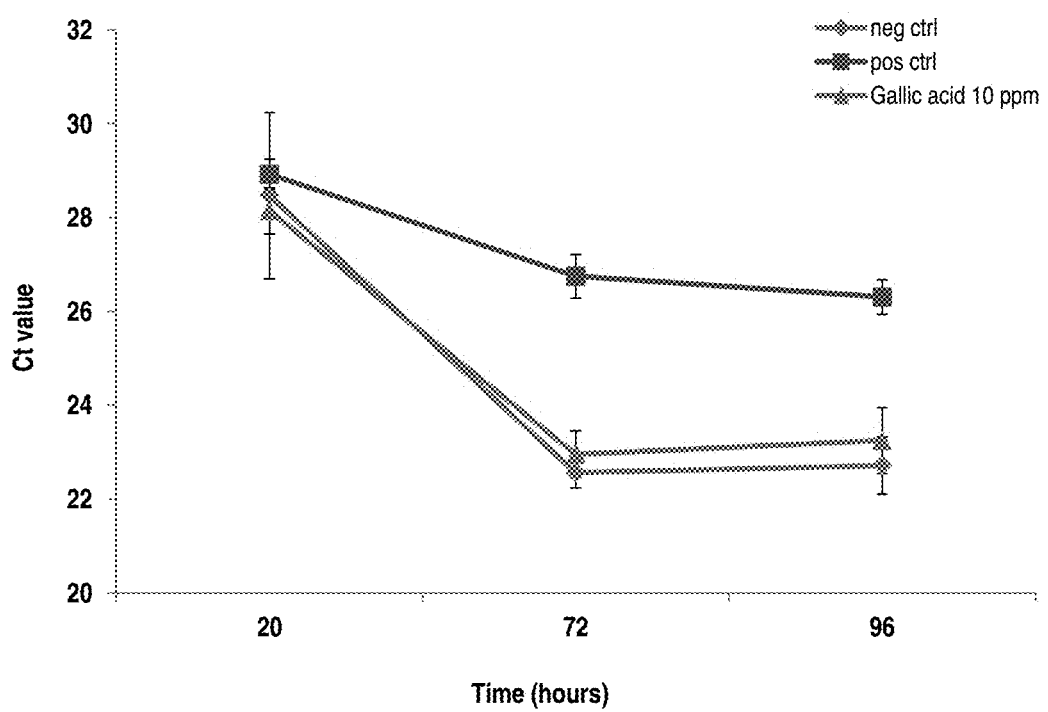
FIG. 16 is a chart of PCR results of MDBK host cells, pre-treated with 10 ppm gallic acid, invaded with sporozoites.

At the different collection time points, DNA was extracted from the MDBK cells. Real-time PCR to detect *Eimeria* DNA was performed on the samples for the different time points and different treatments. The PCR results are presented in FIG. 16.

Real-time PCR analyses

Differences in Ct values were calculated for each time point versus T20 within one treatment (ΔCt). Fold changes were calculated for each time point versus T20 using the following equation:

$$\text{Fold change} = 2^{-\Delta Ct}$$

Figure 17:
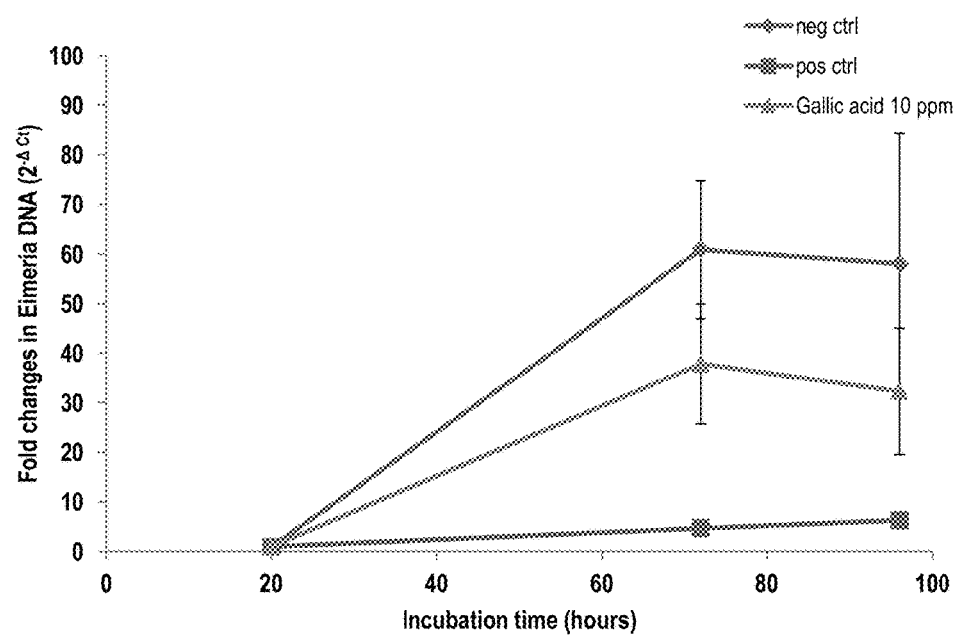
FIG. 17 is a chart of fold changes in *Eimeria* DNA for different time points versus T20 within one treatment.

These results are presented in FIG. 17.

The negative control shows a clear *Eimeria* proliferation since there is a 60 fold increase in *Eimeria* DNA at 96 hours versus the start at 20 hours. The positive control was able to inhibit the proliferation almost completely. Also for 10 ppm gallic acid treatment, a clear inhibition of the proliferation was observed in a dose dependent manner. This indicates that gallic acid at a low dose of 10 ppm is able to protect the host cells to some extend against *Eimeria* proliferation.

Example 9

In vitro effect of gallic acid on *Eimeria tenella* sporozoite invasion and proliferation in host cells An experiment was conducted to evaluate the in vitro effect of gallic acid monohydrate on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 10, 25 and 50 ppm gallic acid monohydrate for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 18:
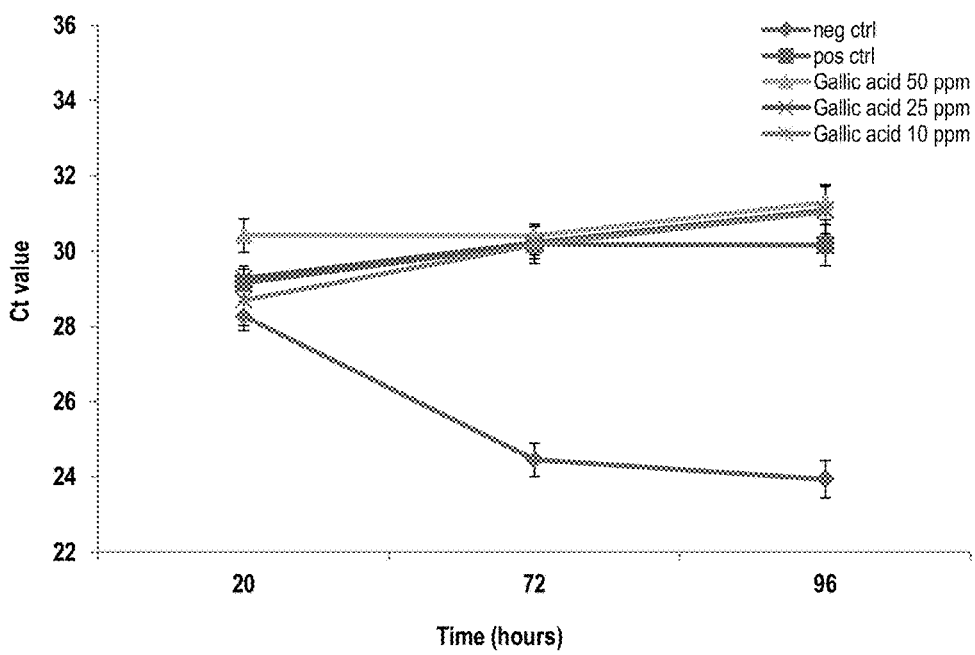
FIG. 18 is a chart of PCR results after invasion of MDBK host cells with sporozoites, pre-treated with different concentrations of gallic acid.

At the different collection time points, DNA was extracted from the MDBK cells. Real-time PCR to detect *Eimeria* DNA was performed on the samples for the different time points and different treatments. The PCR results are presented in FIG. 18.

Real-time PCR analyses

Differences in Ct values were calculated for each time point versus T20 within one treatment (ΔCt). Fold changes were calculated for each time point versus T20 using the following equation:

Fold change=$2^{-\Delta Ct}$

Figure 19:
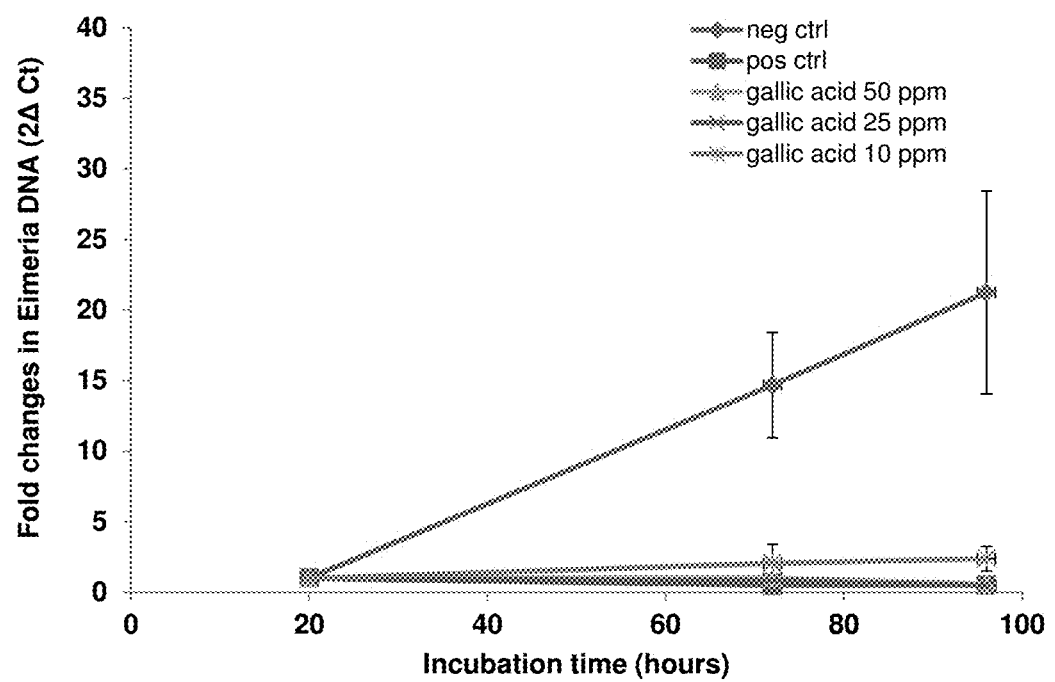
FIG. 19 is a chart of fold changes in *Eimeria* DNA for different time points versus T20 within one treatment.

These results are presented in FIG. 19.

The negative control shows a clear *Eimeria* proliferation since there is a 20 fold increase in *Eimeria* DNA at 96 hours versus the start at 20 hours. The positive control as well as the different dosages of gallic acid inhibited the *Eimeria* proliferation. There was a slightly lower effect visible for 10 ppm gallic acid. But this is negligible in comparison to the increase in the negative control.

Example 10

Efficacy of gallic acid in controlling coccidiosis

Figure 20:
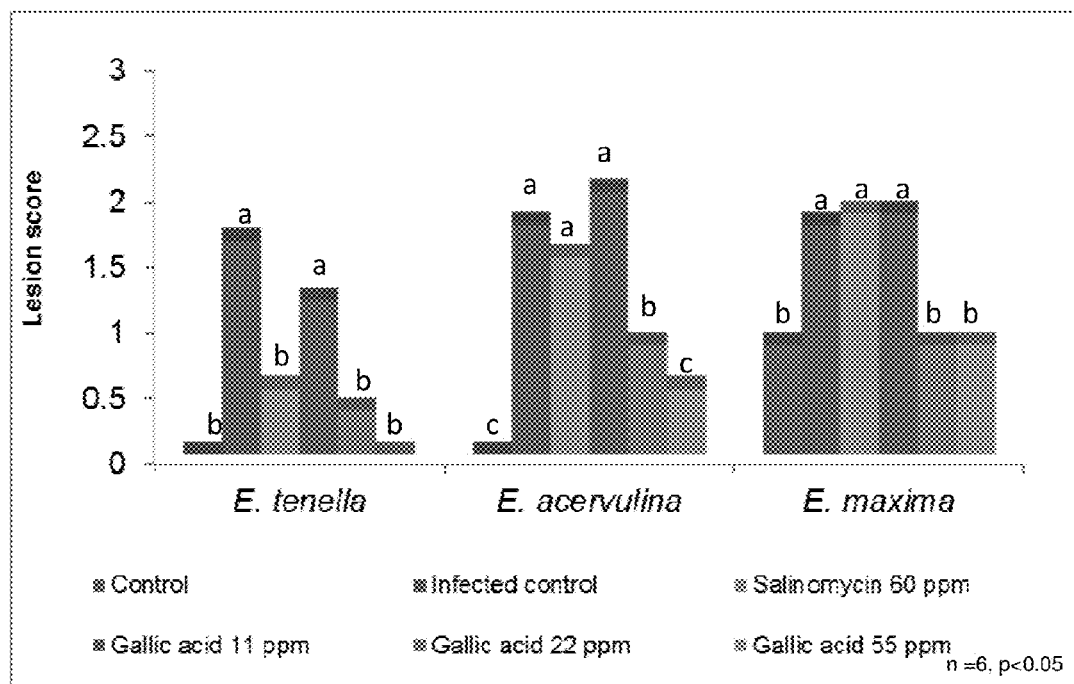
FIG. 20 is a chart of the lesion score on day 5 post infection of birds treated with gallic acid at different concentrations; columns with different superscripts are statistically significant (p<0.05).
Figure 21:
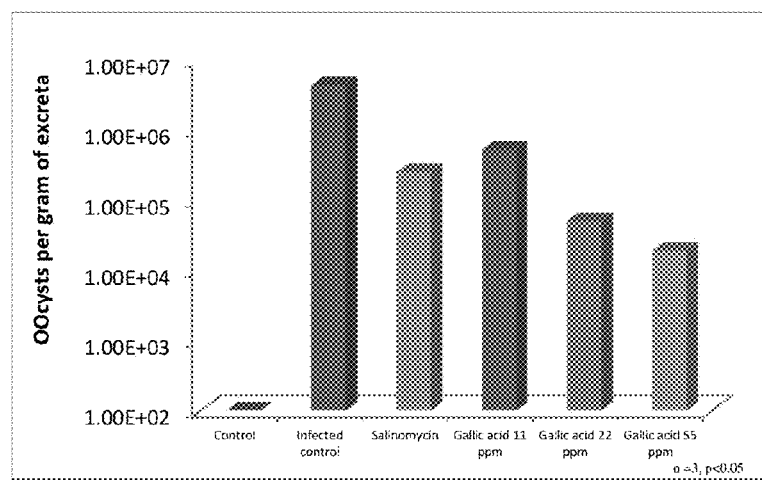
FIG. 21 is a chart of the OPG on day 7 post infection of birds treated with gallic acid at different concentrations; columns with different superscripts are statistically significant (p<0.05).

The efficacy of gallic acid at three different dosages of 11, 22 and 55 ppm in controlling coccidiosis in broiler birds was evaluated by an *in vivo* challenge trial. The birds were induced with mixed infection of Eimeria using oocysts of *E. tenella, E. maxima* and *E. acervulina*. These oocysts were isolated from birds confirmed with clinical coccidiosis. The trial design, oocysts dosage, vaccination schedule, farm maintenance were similar to that of example 3. The lesion scoring showed that there was significant reduction in the score for all the three tested species of Eimeria as compared to the infected control and even the positive control, Salinomycin (FIG. 20). The oocysts per gram showed a similar trend (FIG. 21), however, mortality was not observed in any of the treatment groups including the infected control. Dose dependent response was observed with no signifcant difference between gallic acid at 22 and 55 ppm. This shows that gallic acid is able to control mixed infection of coccidiosis in broiler birds. It is also evident that gallic acid is the active ingredient responsible for the anticoccidial activity of *Q. infectoria*.

Example 11

Anti-sporozoite activity of plants containing gallic acid

Further, other plants that contain gallic acid were also evaluated for their anti-sporozoite activity and anticoccidial activity in broiler birds. The plants chosen were *Rhus chinensis* (Chinese gall nut) and *Terminalia chebula* (Indian gall nut). *Rhus chinensis* contains about 70% hydrolysable tannins and *Terminalia chebula* contains around 0.28% free gallic acid. However, *T. chebula* contains 25 to 40% hydrolysable tannins which can degrade to release gallic acid. These plants have been reported for their antioxidant, anti-inflammatory, antibacterial, antifungal, antimutagenic and anticancer activities.

Figure 22:
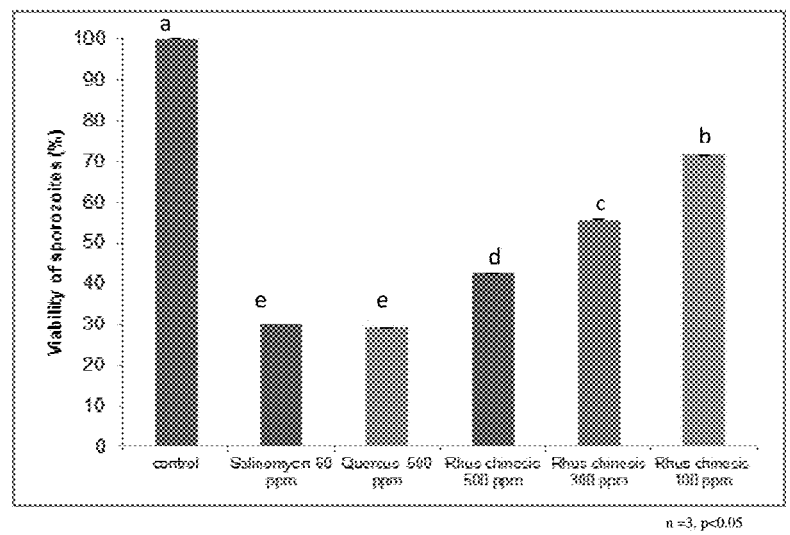
FIG. 22 is a chart of the anti-sporozoite activity of *Rhus chinensis* and *Terminalia chebula*; columns with different superscripts are statistically significant (p<0.05).
Figure 22:
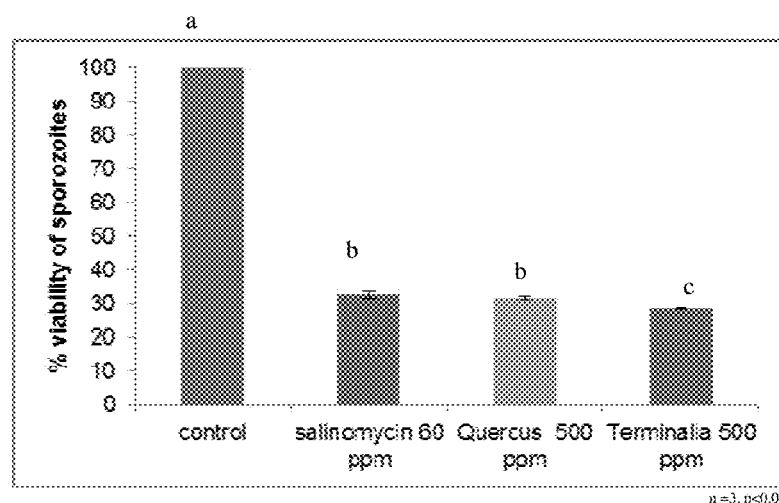

Crude powder of fruit of *Terminalia chebula* and gall nut of *Rhus chinensis* were obtained from Natural Remedies, Bangalore, India and Xinjiang, China respectively. The anti-sporozoite assay by MTT assay showed that both the tested plants were able to reduce the viability of sporozoites as compared to the control and better than the positive control, Salinomycin (FIG. 22).

Example 12

In vitro effect of plants containing gallic acid on *Eimeria tenella* sporozoite invasion and proliferation in host cells An experiment was conducted to evaluate the in vitro effect of other sources of gallic acid on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 50, 100 and 250 ppm of *Terminalia chebula* for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 23:
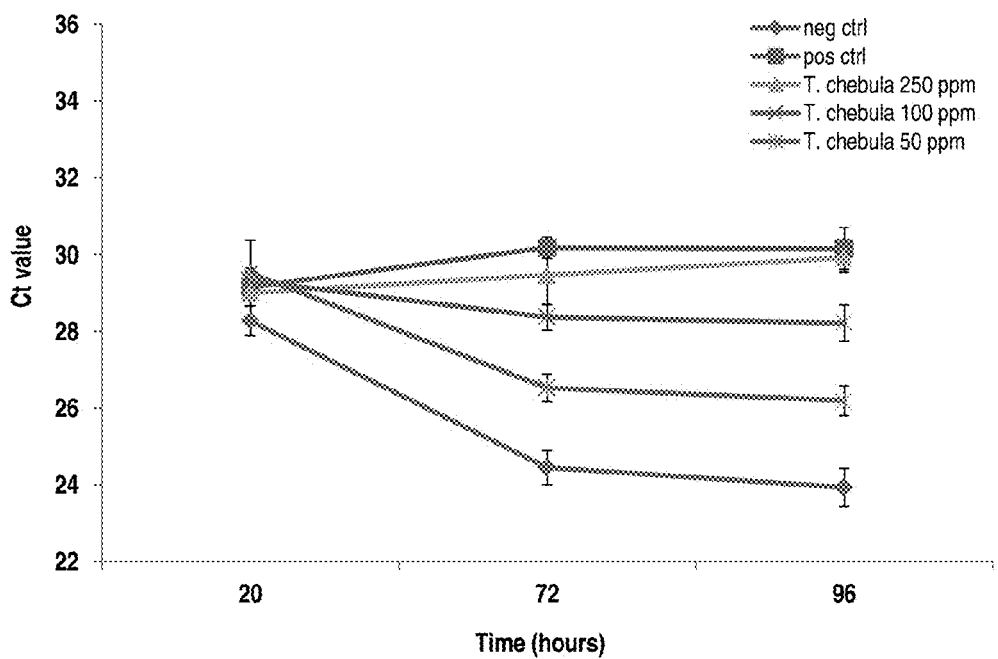
FIG. 23 is a chart of PCR results after invasion of MDBK host cells with sporozoites, pre-treated with different concentrations of *T. chebula*.

At the different collection time points, DNA was extracted from the MDBK cells. Real-time PCR to detect *Eimeria tenella* DNA was performed on the samples for the different time points and different treatments. The PCR results are presented in FIG. 23.

Real-time PCR analyses

Differences in Ct values were calculated for each time point versus T20 within one treatment (ΔCt). Fold changes were calculated for each time point versus T20 using the following equation:

Fold change=$2^{-\Delta Ct}$

Figure 24:
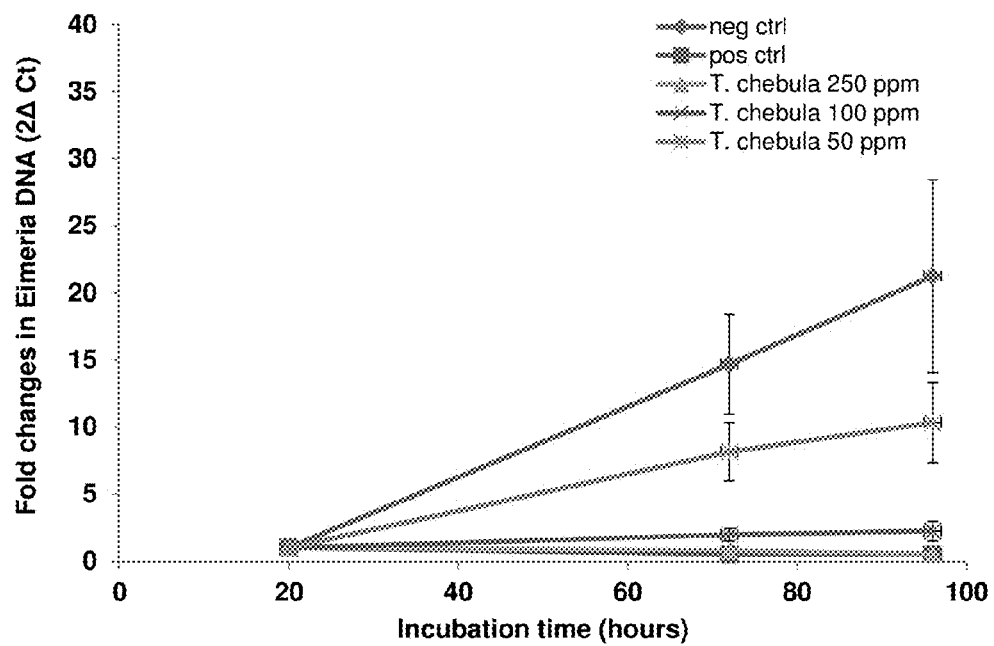
FIG. 24 is a chart of fold changes in *Eimeria* DNA for different time points versus T20 within one treatment.

These results for *T. chebula* are presented in FIG. 24.

The negative control shows a clear *Eimeria* proliferation since there is a 20 fold increase in *Eimeria* DNA at 96 hours versus the start at 20 hours. The positive control as well as 250 ppm *T. chebula* completely inhibited the *Eimeria* proliferation. There was a dose-response effect visible although the lower effect for 100 ppm *T. chebula* is negligible in comparison to the increase in the negative control Example 13

Efficacy of plants containing gallic acid in controlling coccidiosis

Figure 25:
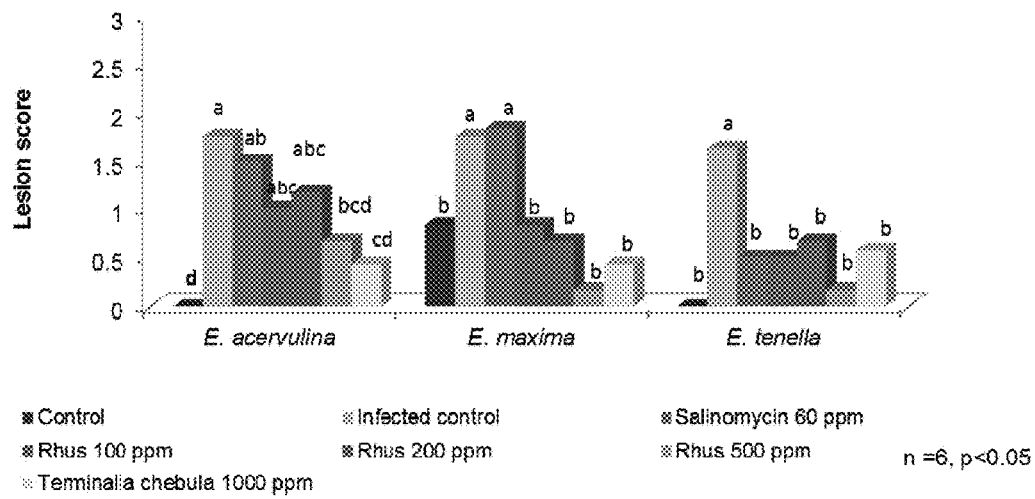
FIG. 25 is a chart of the lesion score on day 5 post infection of birds treated with *R. chinensis* and *T. chebula*; columns with different superscripts are statistically significant (p<0.05).
Figure 26:
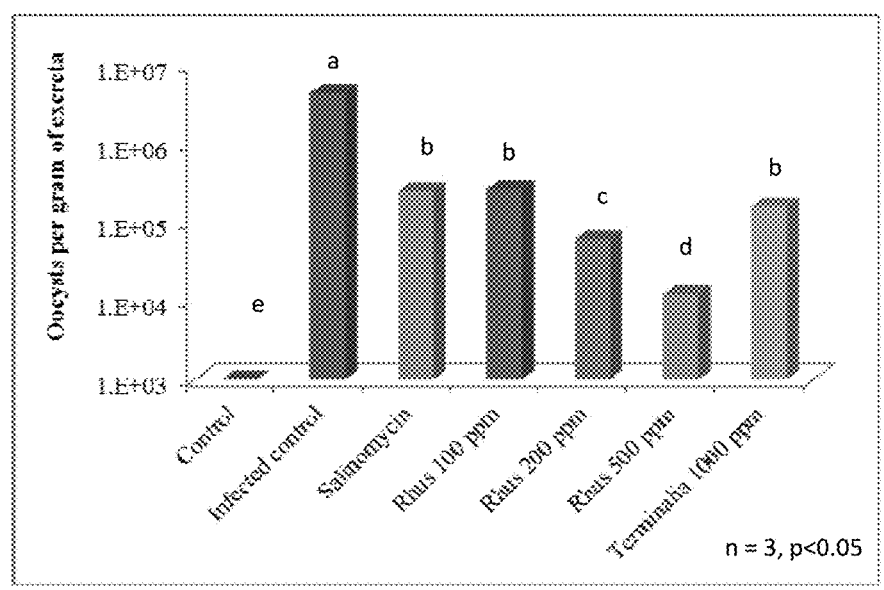
FIG. 26 is a chart of the OPG on day 7 post infection of birds treated with *R. chinensis* and *T. chebula*; columns with different superscripts are statistically significant (p<0.05).

The efficacy of plants containing gallic acid namely, *Terminalia chebula* and *Rhus chinensis* in controlling coccidiosis in broiler birds was evaluated by an in vivo challenge trial. The birds were induced with mixed infection of *Eimeria* using oocysts of *E. tenella, E. maxima* and *E. acervulina* isolated from birds confirmed with clinical coccidiosis. The trial design, oocysts dosage, vaccination schedule, farm maintenance were similar to that of example 3. The lesion scoring showed that *Rhus chinensis* at 200 and 500 ppm and *Terminalia chebula* at 1000 ppm were able to reduce the score for all the three tested species of *Eimeria* as compared to the infected control and even the positive control, Salinomycin (FIG. 25). The oocysts per gram showed a similar trend (FIG. 26), however, mortality was not observed in any of the treatment groups including the infected control. Dose dependent response was observed with *Rhus chinensis*.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of controlling coccidiosis in animals, comprising the step of administering a plant extract to the animal, said plant extract from a plant selected from the group consisting of *Quercus infectoria* and *Rhus chinensis*, said plant extract being administered to the animals in a dose of from about 0.1 to 50 ppm.

2. The method of claim 1, wherein the plant extract is administered to the animals in a dose of from about 2 to 20 ppm.

3. The method of claim 2, wherein the plant extract is administered to the animals in a dose of from about 3 to 10 ppm.

4. The method of claim 1, wherein the coccidiosis is caused by *Eimeria* spp.

5. The method of claim 4, wherein the *Eimeria* spp. are selected from the group consisting of E. tenella, E. maxima and E. acervulina.

6. The method of claim 1, wherein controlling coccidiosis includes a reduction in lesion score, oocysts per gram of fecal matter or mortality.

7. A method of reducing the activity of sporozoites in an animal infected with *Eimeria* spp., comprising the step of administering a plant extract to the animal, said plant extract from a plant selected from the group consisting of *Quercus infectoria* and *Rhus chinensis,* said plant extract being administered to the animals in a dose of from about 0.1 to 50 pp.

8. The method of claim 7, wherein the plant extract is administered in a dose of from about 2 to 20 ppm.

9. The method of claim 8, wherein the plant extract is administered in a dose of from about 3 to 10 ppm.

10. The method of claim 7, wherein the coccidiosis is caused by *Eimeria* spp.

11. The method of claim 10, wherein the *Eimeria* spp. are selected from the group consisting of E. tenella, E. maxima and E. acervulina.

12. The method of claim 7, wherein controlling coccidiosis includes a reduction in lesion score, oocysts per gram of fecal matter or mortality.

13. A method of controlling coccidiosis in animals, comprising the step of administering a plant extract to the animal, said plant extract from *Rhus chinensis* , said plant extract being administered to the animals in a dose of from about 0.1 to 50 ppm.

* * * * *

UNITED STATES PATENT AND TRADEMARK OFFICE
CERTIFICATE OF CORRECTION

PATENT NO. : 10,426,808 B2
APPLICATION NO. : 14/802545
DATED : October 1, 2019
INVENTOR(S) : Gokila Thangavel et al.

Page 1 of 1

It is certified that error appears in the above-identified patent and that said Letters Patent is hereby corrected as shown below:

In the Claims

Column 18, Claim 7, Line 16, "pp." should read --ppm.--.

Signed and Sealed this
Twelfth Day of November, 2019

Andrei Iancu
*Director of the United States Patent and Trademark Office*